United States Patent
Assens et al.

(10) Patent No.: US 6,946,483 B2
(45) Date of Patent: Sep. 20, 2005

(54) AMINOALKENYLBENZOYL-BENZOFURAN OR BENZOTHIOPHENE, METHOD FOR PREPARING SAME AND COMPOSITIONS CONTAINING SAME

(75) Inventors: Jean-Louis Assens, Grabels (FR); Claude Bernhart, Saint Gely du Fesc (FR); Frédérique Cabanel-Haudricourt, Pignan (FR); Victor Dos Santos, Valergues (FR); Patrick Gautier, Cournonterral (FR); Dino Nisato, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/362,291
(22) PCT Filed: Aug. 23, 2001
(86) PCT No.: PCT/FR01/02656
§ 371 (c)(1), (2), (4) Date: Feb. 21, 2003
(87) PCT Pub. No.: WO02/16338
PCT Pub. Date: Feb. 28, 2002

(65) Prior Publication Data
US 2003/0187060 A1 Oct. 2, 2003

(30) Foreign Application Priority Data
Aug. 23, 2000 (FR) ............................... 00 10835

(51) Int. Cl.$^7$ ..................... A61K 31/343; C07D 307/80
(52) U.S. Cl. ..................... 514/469; 349/467; 349/468
(58) Field of Search ..................... 514/469; 549/467, 549/468

(56) References Cited

U.S. PATENT DOCUMENTS

| 5,622,974 A | 4/1997 | Muehl |
| 5,827,876 A | 10/1998 | Sabatucci |

FOREIGN PATENT DOCUMENTS

| WO | WO 96/28152 | 9/1996 |
| WO | WO 97/01549 | 1/1997 |
| WO | WO 99/54325 | 10/1999 |

*Primary Examiner*—Taofiq Solola
(74) *Attorney, Agent, or Firm*—Jiang Lin

(57) ABSTRACT

The invention relates to novel (aminoalkenyl-benzoyl) benzofuran or benzothiophene derivatives of general formula:

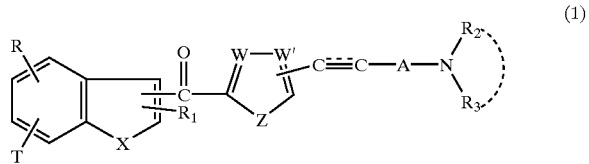

These compounds are of use as medicaments, in particular in the treatment of pathological syndromes of the cardiovascular system.

108 Claims, No Drawings

AMINOALKENYLBENZOYL-BENZOFURAN OR BENZOTHIOPHENE, METHOD FOR PREPARING SAME AND COMPOSITIONS CONTAINING SAME

The present invention relates generally to novel heterocyclic derivatives and to their process of preparation.

More specifically, the invention relates to novel benzofuran or benzothiopene derivatives which can be represented by the general formula:

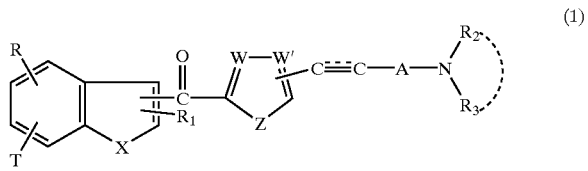

(1)

and to their pharmaceutically acceptable salts, in which:

represents the —CH=CH— group or the

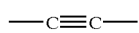

group,

A represents a linear or branched $C_1$–$C_3$ alkylene group or a $C_2$–$C_3$ alkenylene group, T represents hydrogen or a $C_1$–$C_4$ alkyl radical, R represents:

the cyano, hydroxymethyl, formyl or tetrazolyl group, an ester group of general formula:

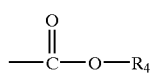

(a)

in which $R_4$ represents a $C_1$–$C_6$ alkyl or $C_3$–$C_6$ cycloalkyl group, a carboxyl group of general formula:

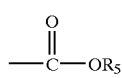

(b)

in which $R_5$ represents hydrogen or an alkali metal atom, an amide group of general formula:

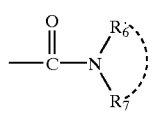

(c)

in which $R_6$ and $R_7$, which are identical or different, represent hydrogen or a linear or branched $C_1$–$C_4$ alkyl radical or $R_6$ and $R_7$, when they are taken together, represent a $C_2$–$C_6$ alkylene chain, a group of general formula:

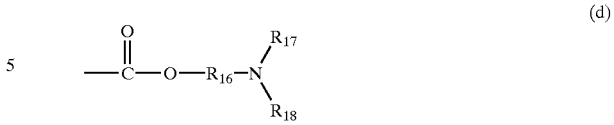

(d)

in which $R_{16}$, $R_{17}$ and $R_{18}$, which are identical or different, represent a linear or branched $C_1$–$C_4$ alkylene group, $R_1$ represents hydrogen, a linear or branched $C_1$–$C_6$ alkyl group, a $C_3$–$C_6$ cycloalkyl group or a phenyl group, $R_2$ and $R_3$, which are identical or different, represent hydrogen, a linear or branched $C_1$–$C_6$ alkyl group or a $C_3$–$C_6$ cycloalkyl group, or $R_2$ and $R_3$, when they are taken together, represent a linear or branched $C_3$–$C_{10}$ alkylene group, these alternatives $R_2$ and $R_3$, which are identical or different, and $R_2$ and $R_3$, taken together, being represented in the formula (1) by the symbol

situated between $R_2$ and $R_3$,

W, W' and Z are such that:

when W and W', which are identical, represent CH, Z represents —O— or —S— when W represents CH and W' represents C—$R_8$, Z represents

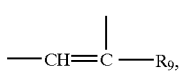

$R_8$ and $R_9$ being identical or different and representing hydrogen, a halogen atom, for example chlorine or bromine, a $C_1$–$C_4$ alkyl radical, such as methyl, or a $C_1$–$C_4$ alkoxy radical, such as methoxy, X represents —O— or —S—, these benzofuran or benzothiphene derivatives being in the form of individual isomers or of mixtures of the latter.

In particular, the benzofuran or benzothiopene derivatives according to the invention are characterized in that

represents the —CH=CH— group.

Classes of preferred compounds of the invention can be represented by the compounds of formula (1);

in which R represents an isopropoxycarbonyl group or in which $R_1$ and/or $R_2$ and/or $R_3$ represent the n-butyl group or in which X represents —O—.

Another class of preferred compounds of formula (1) is that in which

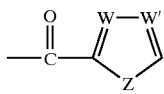

represents the benzoyl radical.

Likewise, a specific class of compounds of formula (1) is that in which the entity:

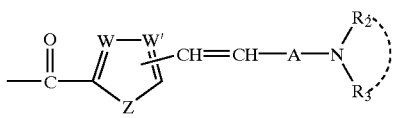

represents a benzoyl radical substituted in the 4-position by a

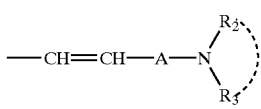

group.

Finally, the compounds of formula (1) in which $R_1$ represents [lacuna] n-butyl [lacuna], A represents the methylene group and $R_2$ and $R_3$, which are identical, represent the n-butyl group can be regarded as preferred.

The compounds of formula (1) can be provided in the form of E or Z geometrical isomers.

Consequently, the invention relates both to the individual isomers of the compounds of formula (1) and to their mixtures.

In addition, the E isomers of the compounds of formula (1) constitute preferred compounds.

The invention also relates to the pharmaceutically acceptable salts of the compounds of formula (1) formed from an organic or inorganic acid.

Mention may be made, as examples of organic salts of this type, of the oxalate, maleate, fumarate, methanesulfonate, benzoate, ascobate, pamoate, succinate, hexamate, bismethylenesalicylate, ethane-disulfonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophylline-acetate, and the salts formed from an amino acid, such as the lysine or histidine salt.

Mention may be made, as inorganic salts of this type, of the hydrochloride, hydrobromide, sulfate, sulfamate, phosphate and nitrate.

Mention may in particular be made of isopropyl 2-butyl-3-[4-[(E)-3-(dibutylamino)-1-propenyl]benzoyl]-1-benzofuran-5-carboxylate hydrochloride.

It has been found that the compounds of the invention possess noteworthy pharmacological properties, in particular antiarrhythmic properties, since they have proved to be capable of suppressing or preventing disorders of the ventricular and auricular rhythm. Most of the compounds of the invention have electrophysiological properties of classes 1, 2, 3 and 4 of the Vaughn-Williams classification, which confer bradycardic, antihypertensive and anti-α-adrenergic and anti-β-adrenergic properties which are noncompetitive. Furthermore, the majority of the compounds have also displayed antioxidizing properties, an affinity for sigma receptors and an ability to enhance the synthesis of NO.

Furthermore, these compounds of the invention demonstrate inhibitory properties with respect to various hormonal agents, such as, for example, angiotensin II, arginine vasopressin, neuropeptide Y or endothelin.

These properties are capable of rendering the compounds in question very useful in the treatment of certain pathological syndromes of the cardiovascular system, in particular in the treatment of angina pectoris, hypertension, arrhythmia, in particular atrial, ventricular or supraventricular arrhythmia, or cerebral circulatory insufficiency. Likewise, the compounds of the invention can be used in the treatment of cardiac insufficiency or myocardial infarction, complicated or not complicated by cardiac insufficiency, or for the prevention of post-infarction mortality.

In the antitumor field, the compounds of the invention may be of use as potentiators of antineoplastics.

Consequently, the invention also relates to a medicament, characterized in that it comprises a compound derived from benzofuran or benzothiophene, or a pharmaceutically acceptable salt of the latter, according to the invention.

Consequently, the invention also relates to pharmaceutical or veterinary compositions comprising, as active principle, at least one compound of the invention in combination with an appropriate excipient or pharmaceutical vehicle.

Depending upon the administration route chosen, the daily dosage for a human being weighing 60 kg will lie between 2 and 2 000 mg of active principle, in particular between 50 and 500 mg of active principle.

The compounds of formula (1) can be prepared according to the following methods:

A.—In the case where R represents the cyano group, the formyl group, a group (a) or a group (c) and when the compound of formula (1) is in the form of an isomer with the E configuration, by reacting a compound of general formula:

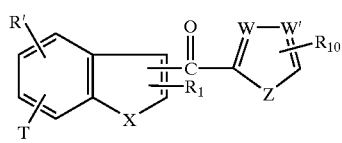

(2)

in which R' represents the cyano group, the formyl group, a group (a) or a group (c), $R_{10}$ represents a halogen atom, preferably bromine or iodine, or the trifluoromethanesulfonyloxy group and $R_1$, T, X, W, W' and Z have the same meaning as above, with an organotin derivative with the E configuration corresponding to the general formula:

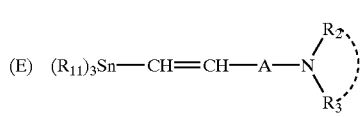

(3)

in which A, $R_2$ and $R_3$ have the same meaning as above and $R_{11}$ represents a $C_1$–$C_4$ alkyl radical, in particular a butyl radical, after protection of the amine functional group when $R_2$ and/or $R_3$ represent hydrogen, this reaction being carried out in the presence of lithium chloride and of an organopalladium derivative, such as tetrakis(triphenylphosphine) palladium, and then by deprotecting, if necessary, the compound thus formed, which gives the desired compounds of formula (1) in the free base form.

Usually, the reaction takes place at the reflux temperature of the solvent, which can, for example, be an ether, such as dioxane.

In addition, the protection of the amine functional group of the compound of formula (3), that is to say the protection envisaged when $R_2$ and/or $R_3$ represent hydrogen, can be obtained, for example, by treatment by means of a compound which makes possible the attachment of a group which can be easily removed, in particular by means of a t-butoxycarbonyl anhydride, and the deprotection is carried out subsequently, in this case, after treatment in an acidic medium.

B.—In the case where R represents the cyano group, the formyl group, a group (a) or a group (c) and when the compound of formula (1) is in the form of an isomer with the Z configuration, by hydrogenating an alkynyl compound of general formula:

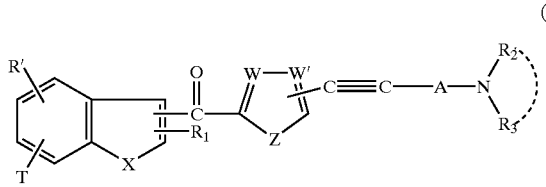

(4)

in which A, R', $R_1$, $R_2$, $R_3$, T, W, W', X and Z have the same meaning as above, this reaction being carried out in the presence of an appropriate catalyst, such as palladium-on-charcoal, which gives the desired compounds of formula (1) in the free base form.

Usually, the reaction is carried out in a solvent, such as an aromatic hydrocarbon, for example toluene, and at ambient temperature.

C.—In the case where R represents a group (b), by saponifying a compound of formula (1) as above in which R represents a group (a), that is to say a compound of general formula:

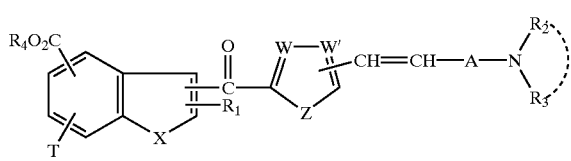

(5)

in which A, $R_1$, $R_2$, $R_3$, $R_4$, T, W, W' and Z have the same meaning as above, in the presence of a basic agent, namely an alkali metal hydroxide, for example sodium hydroxide, which gives, in the free base form, the compounds of formula (1) in which $R_5$ represents an alkali metal atom, which compounds are treated, if necessary, with a strong acid, for example hydrochloric acid, which gives, in the free base form, the desired compounds of formula (1) in which $R_5$ represents hydrogen.

D.—In the case where R represents the hydroxymethyl group, by deprotecting a ketal of general formula:

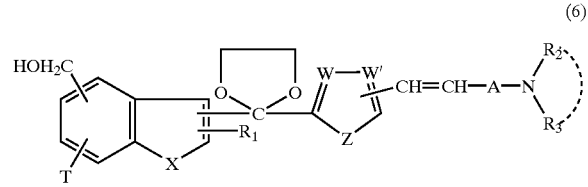

(6)

in which A, $R_1$, $R_2$, $R_3$, T, X, W, W' and Z have the same meaning as above, this reaction being carried out by means of pyridine p-toluenesulfonate and preferably at the reflux temperature, which gives the desired compounds of formula (1) in the free base form.

The benzofuran or benzothiophene derivatives of formula (1) which also correspond to the general formula:

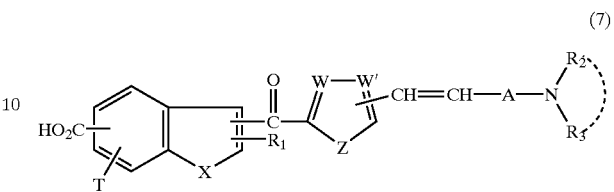

(7)

in which A, $R_1$, $R_2$, $R_3$, T, W, W', X and Z have the same meaning as above, are themselves synthetic intermediates for the preparation of compounds of formula (1).

E.—For example, the compounds of formula (1) in which R represents a group (c) in which $R_6$ and $R_7$ are identical and each represent hydrogen can be prepared alternatively by reacting a compound of formula (7) in question by means of dicyclohexylcarbodiimide in the presence of hydroxybenzotriazole and of ammonia, which gives the desired compounds of formula (1) in the free base form.

Other compounds of formula (1) can be used as intermediates in the synthesis of compounds of the invention, in particular the cyano derivatives which also correspond to the general formula:

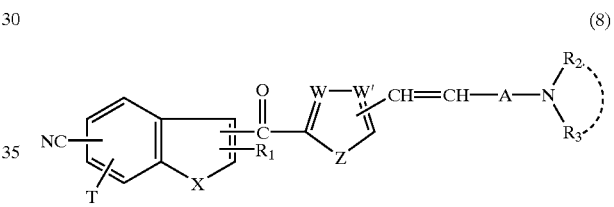

(8)

in which A, $R_1$, $R_2$, $R_3$, T, W, W', X and Z have the same meaning as above.

Thus, use may be made of the following methods, that is to say:

F.—In the case where R represents a group (c) in which $R_6$ and $R_7$ each represent hydrogen, a compound of formula (8) is hydrolyzed in the presence of a strong acid, such as, for example, sulfuric acid, and generally at ambient temperature, which gives the desired compounds of formula (1) in the free base form.

G.—In the case where R represents the tetrazolyl group, a compound of formula (8) is reacted, preferably in an aprotic solvent, such as an aromatic hydrocarbon, for example benzene or toluene, and usually at the reflux temperature of the medium, with a [tri($C_1$–$C_4$ alkyl)] azidotin, for example tributyltin azide, which gives the desired compounds of formula (1) in the free base form.

The methods described above make it possible to obtain the compounds of formula (1) in the form of individual E or Z isomers or in the form of mixtures of the latter, according to the process employed.

If necessary, these isomers can be produced in the separate form from their mixtures by employing known methods, such as, for example, chromatography or precipitation.

H.—The compounds of formula (1) obtained in the free base form according to one or other of the methods described above can subsequently be converted, if necessary, to pharmaceutically acceptable salts by reaction with an appropriate organic or inorganic acid, for example oxalic, maleic, fumaric, methanesulfonic, benzoic, ascorbic, pamoic, succinic, hexamic, bismethylenesalicylic, ethanedisulfonic, acetic, propionic, tartaric, salicylic, citric, gluconic, lactic, malic, cinnamic, mandelic, citraconic, aspartic, palmitic, stearic, itaconic, glycolic, p-aminobenzoic, glutamic, benzenesulfonic, p-toluene-sulfonic or theophyllineacetic acid, lysine or histidine, or hydrochloric, hydrobromic, sulfuric, sulfamic, phosphoric or nitric acid.

The compounds of formula (2) can be obtained:

a) when $R_{10}$ represents a halogen atom, by reacting a compound of general formula:

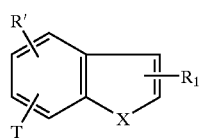

(9)

in which R', $R_1$ and T have the same meaning as above, with a halide of general formula:

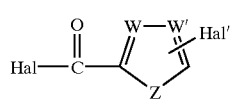

(10)

in which W, W' and Z have the same meaning as above and Hal and Hal', which are identical or different, represent a halogen atom, preferably bromine or iodine, this reaction being carried out in the presence of a Lewis acid, such as aluminum chloride, ferric chloride or stannic chloride, to form the desired compounds of formula (2);

b) when $R_{10}$ represents a trifluoromethane-sulfonyloxy group, by reacting a compound of general formula:

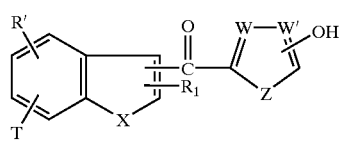

(11)

in which R', $R_1$, T, W, W', X and Z have the same meaning as above, this reaction being carried out with trifluoromethanesulfonic anhydride in the presence of an acid acceptor, such as pyridine, which gives the desired compounds of formula (2).

As regards the tin compounds of formula (3), they can be obtained by reacting an alkynylamine of general formula:

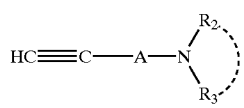

(12)

in which A, $R_2$ and $R_3$ have the same meaning as above, after protection of the amine functional group when $R_2$ and/or $R_3$ represent hydrogen, this reaction being carried out with a hydride of general formula:

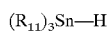

(13)

$(R_{11})_3Sn—H$ in which $R_{11}$ has the same meaning as above, which gives the desired compounds of formula (3).

With regard to the compounds of formula (4), they can be prepared by reacting a compound of formula (2) with an alkyne derivative of formula (12), after protection of the amine functional group when $R_2$ and/or $R_3$ represent hydrogen, this reaction being carried out in the presence of an organopalladium compound as catalyst, essentially a salt of palladium(II) preferably complexed with at least one organophosphorus compound comprising trivalent phosphorus, for example dichlorobis(triphenylphosphine) palladium, and then, if necessary, the compound thus formed is deprotected, which gives the desired compounds of formula (4).

The protection of the amine functional group of the compound of formula (12), that is to say the protection envisaged when $R_2$ and/or $R_3$ represent hydrogen, can be obtained, for example, by treatment by means of a compound which makes possible the attachment of a group which can be easily removed in particular by means of a t-butyoxycarbonyl anhydride, and the deprotection is carried out subsequently, in this case, by treatment in an acidic medium.

The compounds of formula (6) can be prepared starting from an ester of formula (1) in which R represents a group (a):

(a) by treating this ester of formula (1) at the reflux temperature of the medium with glycol in the presence of p-toluenesulfonic acid, to form a diether of general formula:

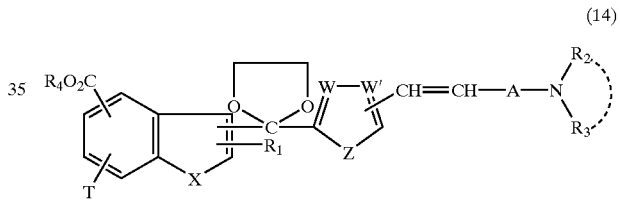

(14)

in which A, $R_1$, $R_2$, $R_3$, $R_4$, T, X, W, W' and Z have the same meaning as above, (b) by reducing this compound of formula (14) by means of an alkali metal hydride, such as lithium aluminum hydride, and in a solvent, such as an ether, to produce the desired compounds.

The compounds of formula (9) in which R' is situated in the 5-position and represents the cyano group or a group (a) and $R_1$ is situated in the 2-position can be prepared according to the sequence of stages below:

a) either, a cyano derivative of general formula:

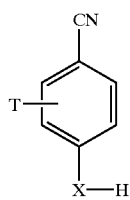

(15)

in which T and X have the same meaning as above, is treated with iodine in the presence of ammonia to form an iodo derivative of general formula:

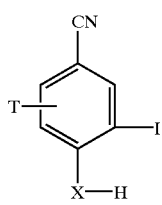
(16)

in which T and X have the same meaning as above, or, a benzoic acid derivative of general formula:

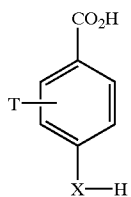
(17)

in which T and X have the same meaning as above, is treated first with an alkali metal iodide and an oxidizing agent, such as an alkali metal hypochlorite, for example sodium hypochlorite, and subsequently with an alcohol of general formula:

$$R_4\text{—OH} \quad (18)$$

in which $R_4$ has the same meaning as above, which gives an iodo derivative of general formula:

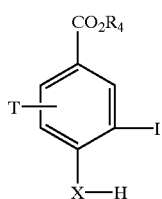
(19)

in which $R_4$, T and X have the same meaning as above,
b) the iodinated derivative of formula (16) or (19) is reacted with an acetylenic derivative of general formula:

$$HC\equiv C\text{—}R_1 \quad (20)$$

in which $R_1$ has the same meaning as above, this reaction being carried out in the presence of an appropriate catalyst, such as a palladium derivative, for example tetrakis(triphenylphosphine)palladium, and of cuprous iodide, which gives the desired compounds of formula (2).

If necessary, the preparation of the ester of formula (19) can be carried out according to the method described above but starting from an acid of formula (17) in the acyl halide form obtained after treatment of the benzoic acid derivative of formula (17) by means of a halogenating agent, for example thionyl chloride, phosgene or oxalyl chloride.

B.—The compounds of formula (9) in which R' is situated in the 6-position and represents the cyano group or a group (a) and $R_1$ is situated in the 2-position can be obtained as follows:

a) a compound of general formula:

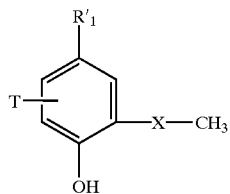
(21)

in which T and X have the same meaning as above and $R'_1$ represents the cyano group or a group (a), is reacted with trifluoromethanesulfonic anhydride in the presence of pyridine, to produce a compound of general formula:

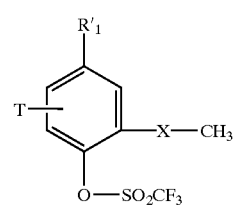
(22)

in which $R'_1$, T and X have the same meaning as above,
b) the compound thus formed is reacted with an acetylenic derivative of formula (20), this reaction being carried out in the presence of an appropriate catalyst, for example a palladium derivative, such as dichlorobis(triphenylphosphine)palladium, and of an acid acceptor, such as triethylamine, to form the compounds of general formula:

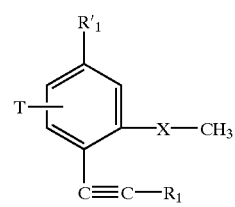
(23)

in which $R'_1$, $R_1$, T and X have the same meaning as above,
c) this compound of formula (23) is then cyclized in the presence of boron tribromide at a temperature of less than −50° C., which gives the heterocyclic compounds of general formula:

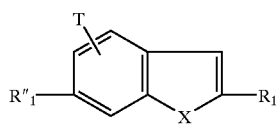
(24)

in which $R_1$, T and X have the same meaning as above and $R''_1$ represents the cyano or carboxylic group, which gives either desired compounds of formula (9) when $R''_1$ represents the cyano group or an acid when $R''_1$ represents the carboxylic group,
d) this acid is esterified with an alcohol of formula (18), which gives desired compounds of formula (9).

C.—The compounds of formula (9) in which R' is situated in the 4-position and represents the cyano group or a group (a) and $R_1$ is situated in the 2-position can be obtained as follows:

a) a compound of general formula:

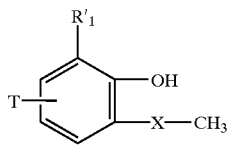
(25)

in which R'$_1$, T and X have the same meaning as above, is reacted with trifluoromethanesulfonic acid in the presence of pyridine, to produce a compound of general formula:

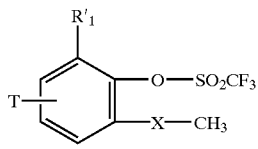
(26)

in which R'$_1$, T and X have the same meaning as above, b) the compound thus formed is reacted with an acetylenic derivative of formula (20), this reaction being carried out in the presence of an appropriate catalyst, such as a palladium derivative, for example dichlorobis(triphenylphosphine) palladium, and of an acid acceptor, such as triethylamine, to form the compounds of general formula:

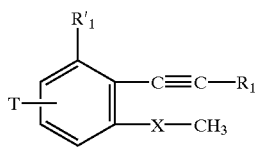
(27)

in which R'$_1$, R$_1$ and X have the same meaning as above, c) this compound of formula (27) is then cyclized in the presence of boron tribromide, which gives the heterocyclic compounds of general formula:

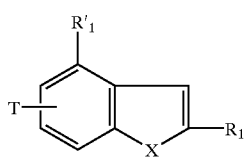
(28)

in which R'$_1$, R$_1$, T and X have the same meaning as above, which correspond to the desired compounds of formula (9).

Alternatively, the compounds of formula (9) in which R' is situated in the 5-position and represents the cyano group or a group (a) and R$_1$ is in the 2-position can also be prepared as follows:

I. When R' represents a group (a):
a) a benzoate of general formula:

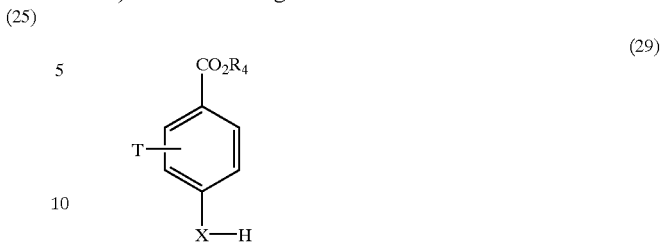
(29)

in which R$_4$, T and X have the same meaning as above, is first treated with methanesulfonic acid in the presence of phosphorus pentoxide and hexamethylenetetraamine, to give a formyl derivative of general formula:

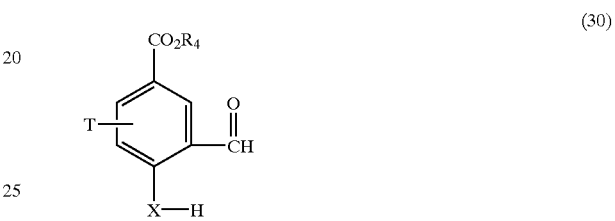
(30)

in which R$_4$, T and X have the same meaning as above,
b) this compound of formula (30) is subsequently reacted with an ester of general formula:

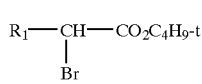
(31)

in which R$_1$ has the same meaning as above, which gives the compounds of general formula:

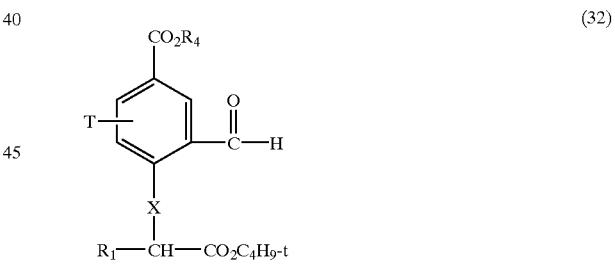
(32)

in which R$_1$, R$_4$, T and X have the same meaning as above,
c) this ester of formula (32) is treated with formic acid or trifluoroacetic acid, which gives the acids of general formula:

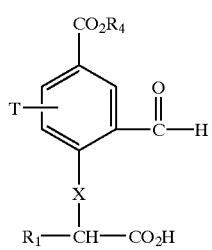
(33)

in which $R_1$, $R_4$, T and X have the same meaning as above, d) this compound (33) is cyclized in the presence of benzenesulfonyl chloride or p-toluene-sulfonyl chloride and of an acid acceptor, such as triethylamine, which gives the desired compounds of formula (9).

II. When R' represents the cyano group:

a) a formyl derivative of general formula:

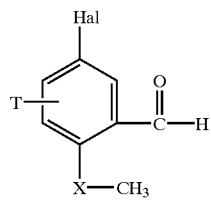
(34)

in which Hal, T and X have the same meaning as above, is first treated with zinc cyanide in the presence of an appropriate catalyst, for example a palladium derivative, such as tetrakis(triphenylphosphine)-palladium, which gives the compounds of general formula:

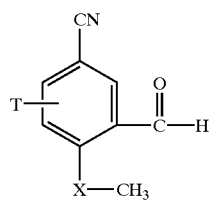
(35)

in which T and X have the same meaning as above, b) this compound of formula (35) is subsequently demethylated with lithium chloride, which gives the compounds of general formula:

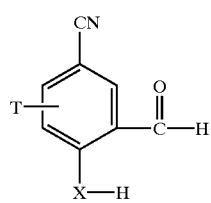
(36)

in which T and X have has the same meaning as above, c) this compound of formula (36) is then treated with an ester of general formula:

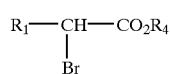
(37)

in which $R_1$ and $R_4$ have the same meaning as above, this reaction being carried out in the presence of a basic agent, such as an alkali metal carbonate, which gives the compounds of general formula:

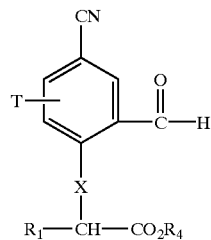
(38)

in which $R_1$, $R_4$, T and X have the same meaning as above, d) and e) this ester of formula (38) is saponified in the presence of a basic agent, such as an alkali metal hydroxide, and the acid thus obtained is cyclized in the presence of benzenesulfonyl chloride or p-toluenesulfonyl chloride and of an acid acceptor, such as triethylamine, which gives the desired compounds.

The compounds of formula (9) in which R' is situated in the 7-position and represents the cyano group or a group (a) and $R_1$ is situated in the 2-position can be obtained according to the sequence of stages below:

a) an alcohol of general formula:

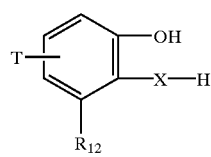
(39)

in which $R_{12}$ represents a cyano or formyl group and T and X have the same meaning as above, is treated, this reaction being carried out with methyl iodide in the presence of an alkali metal hydride, to give a compound of general formula:

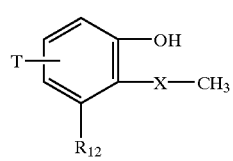
(40)

in which $R_{12}$, T and X have the same meaning as above, b) the compound thus formed is reacted with trifluoromethanesulfonic anhydride, to form a compound of general formula:

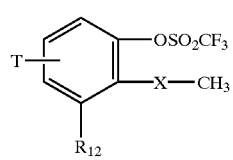
(41)

in which $R_{12}$, T and X have the same meaning as above, c) the compound thus formed is treated with a compound of formula (20) in the presence of an appropriate catalyst, such as a palladium derivative, for example dichlorobis(triphenylphosphine)palladium which produces the compound of general formula:

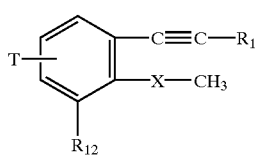

(42)

in which $R_1$, $R_{12}$, T and X have the same meaning as above, d) the compound of formula (42) thus formed is subsequently reacted:

when $R_{12}$ represents the cyano group, with lithium chloride, to form the desired compounds of formula (9) in which R' represents the cyano group, when $R_{12}$ represents the formyl group, with an alkali metal cyanide in the presence of manganous oxide and acetic acid, to give a compound of general formula:

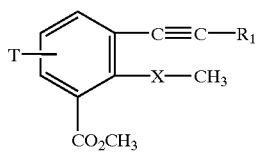

(43)

in which $R_1$, T and X have the same meaning as above, which is cyclized with lithium chloride, to give a mixture of ester and of acid of general formula:

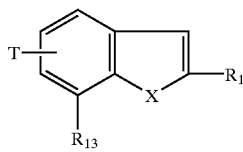

(44)

in which $R_1$, X and T have the same meaning as above and $R_{13}$ represents the methoxycarbonyl or carboxylic group, which mixture is treated with methanol in the presence of a strong acid, such as sulfuric acid, which gives the desired compounds of formula (9) in which R' represents the methoxycarbonyl group.

The other compounds of formula (9), that is to say the compounds of formula (9) in which R', situated in the 7-position, represents a group (a), with the exception of the methoxycarbonyl group, can be obtained by saponifying an ester of formula (9) in which R', situated in the 7-position, represents the methoxycarbonyl group, this reaction being carried out in the presence of a basic agent, such as an alkali metal hydroxide, to give a salt, which is acidified with a strong acid, such as hydrochloric acid, to give a 7-carboxybenzofuran derivative, which is esterified with an alcohol of general formula:

R'$_4$—OH (45)

in which R'$_4$ represents a $C_2$–$C_6$ alkyl group or a $C_3$–$C_6$ cycloalkyl group, which gives the desired compounds of formula (9).

The compounds of formula (9) in which R' represents the formyl group can be prepared by oxidizing, with oxalyl chloride, an alcohol of general formula:

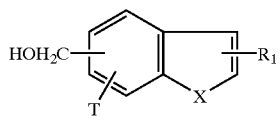

(46)

in which $R_1$, T and X have the same meaning as above, to give the desired compounds.

Likewise, the compounds of formula (9) in which R' represents a group (c) can be obtained by:

saponifying an ester of formula (9) in which R' represents a group (a), this reaction being carried out by means of an alkali metal hydroxide, to produce an alkali metal derivative, treating the alkali metal derivative in question with a strong acid, such as hydrochloric acid, to form an acid, halogenating this acid by means of an appropriate halogenating agent, such as thionyl chloride, to produce an acyl halide, by amidating the acyl halide thus obtained, this reaction being carried out by means of a compound of general formula:

(47)

in which $R_6$ and $R_7$ have the same meaning as above, to form the desired compounds of formula (9).

The compounds of formula (10) can be obtained with the sequence of stages below:

a) acylation of a compound of general formula:

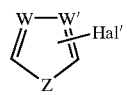

(48)

in which Hal', W, W' and Z have the same meaning as above, with acetyl chloride, this reaction being carried out in the presence of a Lewis acid, such as aluminum chloride, to form a compound of general formula:

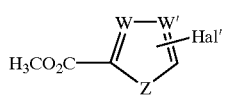

(49)

in which Hal', W, W' and Z have the same meaning as above, b) reaction of the compound thus formed, first with bromine in the presence of an alkali metal hydroxide and subsequently with a strong acid, such as hydrochloric or sulfuric acid, to produce the acids of general formula:

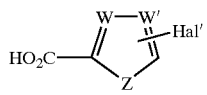

(50)

in which Hal', W, W' and Z have the same meaning as above, c) halogenation of the acid thus formed by treatment by means, for example, of thionyl chloride, to produce the desired compounds of formula (10).

As regards the compounds of formula (11), they can be obtained by reacting a benzofuran or benzothiophene derivative of formula (9) [lacuna] a halide of general formula:

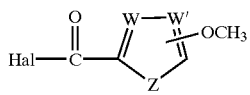
(51)

in which Hal represents a halogen atom, such as chlorine or bromine, this reaction being carried out in the presence of a Lewis acid as catalyst, for example ferric chloride, aluminum chloride or tin tetrachloride, which gives the methoxy derivatives of general formula:

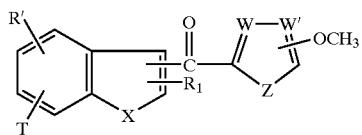
(52)

in which R', $R_1$, T, W, W', X and Z have the same meaning as above, which methoxy derivatives are demethylated by heating in the presence, for example, of aluminum chloride, to form the desired compounds.

Alternatively, the compounds of formula (11) or of formula (52) in which R' represents a group (a), a group (b) or a group (c) can be obtained for employing various methods, according to which:

an ester of general formula:

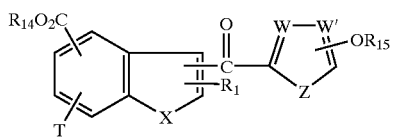
(53)

in which $R_1$, T, W, W'X and Z have the same meaning as above, $R_{14}$ represents a $C_1$–$C_4$ alkyl radical, preferably methyl or ethyl, and $R_{15}$ represents hydrogen or the methyl radical, is saponified, this reaction being carried out with an alkali metal hydroxide, to produce the compounds of formula (11) or of formula (52) in which R' represents a group (b) in which $R_6$ represents an alkali metal atom, the alkali metal derivative thus formed is treated with a strong acid, such as hydrochloric acid, to produce an acid, that is to say the compounds of formula (11) or of formula (52) in which R' represents a group (b) in which $R_6$ represents hydrogen, the acid thus formed is treated:
either: a) with a halogenating agent, such as thionyl chloride, to produce an acyl chloride, which is esterified with an alcohol of formula (18), or
b) with an alcohol of formula (18) in the presence of a strong acid as catalyst, for example sulfuric acid, to produce the compounds of formula (11) or of formula (51) in which R' represents a group (a),
or: with a halogenating agent, such as thionyl chloride, to produce an acyl chloride, which is amidated with a compound of formula (47), to produce the compounds of formula (11) or of formula (52) in which R' represents a group (c).

The other starting compounds or intermediates involved in the various processes described above are for the most part known compounds or compounds which can be prepared by known methods.

Benzothiophene derivatives comprising a 1-alkenylbenzoyl chain and which are variously substituted on the homocycle are already known. Such compounds have been disclosed, for example, in patents or patent applications U.S. Pat. No. 5,827,876 or WO 97/01549, where they are presented as possessing inhibiting properties with respect to bone loss or properties for the treatment of symptoms of the menopause or for the treatment of restenosis.

In point of fact, it has now been discovered, in the context of the invention, that benzofuran or benzothiophene derivatives comprising an aminoalkenyl-benzoyl chain and other groups attached to the heterocycle via a carbon atom exhibit highly advantageous pharmacological properties, in particular antiarrhythmic properties, while offering very good metabolic stability, highly acceptable solubility and very good bioavailability via the oral route.

The results of pharmacological tests carried out for the purpose of determining properties of the compounds of the invention with respect to the cardiovascular system are listed below.

I. Ventricular Arrhythmias

The aim of this test is to determine the ability of the compounds of the invention to provide protection against arrhythmias brought about by reperfusion. To this end, use was made of the method reported by Manning A. S. et al. in Circ. Res., 1984, 55, 545–548, modified as follows: Rats, divided into batches, are first anaesthetized with sodium pentobarbital (60 mg/kg via the intraperitoneal route) and then they are intubated and maintained under assisted respiration.

A cannula for intravenous administration is subsequently inserted in their right jugular veins, an intravenous dose of the compound to be studied is administered and, 5 minutes later, a ligature loop is placed around the left anterior descending coronary artery in the immediate proximity of its origin. This artery is then occluded for 5 minutes by pulling on the ends of the ligature, so as to induce reperfusion by relaxing the tension.

The arrhythmias induced by this reperfusion are then evaluated.

An analogous test was carried out by the oral route. In this case, the compound to be studied is administered 120 minutes before ligating the left anterior descending coronary artery.

The results of these tests showed that the compounds of the invention significantly protect the treated animals, ranging up to 100% at doses of between 0.3 and 10 mg/kg via the intravenous route and 10 to 90 mg/kg via the oral route.

II. Antiadrenergic Properties

The aim of this test is to determine the ability of the compounds of the invention to reduce the increase in blood pressure induced by phenylephrine (anti-α effect) and the acceleration in heart rate induced by isoprenaline (anti-β effect) in dogs anaesthetized beforehand with pentobarbital and chloralose.

For each dog, the dose of phenylephrine (5 or 10 µg/kg) which leads to an increase in the arterial pressure of between 25 and 40 mmHg and the dose of isoprenaline (0.9 or 1 µg/kg) which should lead to an increase in the heart rate of between 60 and 120 beats/minute are first determined.

The doses of phenylephrine and of isoprenaline thus determined are injected alternately every 10 minutes and, after obtaining 2 successive reference responses, a dose of the compound to be studied is administered via the intravenous route.

Anti-α Effect

The percentage of reduction, by the compound of the invention, in the induced hypertension, in comparison with the reference hypertension obtained before injection of this compound (approximately 100 mmHg), is recorded.

Anti-β Effect

The percentage of reduction, by the compound to be studied, in the induced acceleration of the heart rate is recorded.

The results of these tests show that, at doses varying from 1 to 10 mg/kg, the compounds of the invention exhibit anti-α and/or anti-β effects which are reflected by reductions ranging from 50% to virtually 100% in the induced hypertension and/or in the induced increase of the heart rate.

III. Auricular Fibrillation

The aim of this test is to evaluate the effectiveness of the compounds of the invention with respect to auricular fibrillation induced by permanent stimulation of the vagus nerve in the anaesthetized dog according to the method described in Circulation, 1993, 88, 1030–1044. The compounds to be studied are administered at the cumulative doses of 3 and 10 mg/kg in slow intravenous infusions of 10 minutes during an episode of sustained auricular fibrillation. At the dose of 10 mg/kg, the compounds of the invention generally convert 100% of the auricular fibrillations into a sinus rhythm and prevent the reinduction thereof in 50 to 100% of cases. At this dose, significant increases in the heart period and auricular effective refractory periods for various basal values of the heart period are observed.

IV. Inhibiting Effects on the Neurohormonal System

The aim of this test is to look for inhibiting effects of the compounds of the invention with respect to vasoconstrictive effects induced by various peptides, such as noradrenaline (NA), angiotensin II (A-II), arginine vasopressin (AVP), neuropeptide Y (NPY) and endothelin (ET), and also with respect to tachycardic effects induced by isoprenaline (Iso) in the conscious rat.

An arterial catheter (right carotid artery), for the measurement of the arterial pressure, and a venous catheter (right jugular vein), for the injection of the products to be studied, are implanted, 24 hours before the test, in male Sprague Dawley rats weighing approximately 300 g. On the following day, the rats are placed in cylindrical cages and the arterial catheter is connected to a pressure sensor via a revolving joint on a pendulum. This pressure sensor is itself connected to a polygraph for recording the arterial pressure.

The action of the compounds of the invention, via the intravenous route, is then investigated with respect to vasoconstrictive effects induced by NA (1 µg/kg), A-II (100 µg/kg) and AVP (40 µg/kg) at the respective doses of either 3, 10 and 30 mg/kg or 1.3 to 10 mg/kg and solely at the dose of 10 mg/kg with respect to vasoconstrictive effects induced by NPY (6 µg/kg) and ET (0.5 µg/kg) or tachycardic effects induced by Iso (1 µg/kg).

First, the various peptide agonists are dissolved in 0.9% physiological saline and the compound to be studied is dissolved in an appropriate solvent. These peptides are subsequently injected as a bolus under a volume of 0.05 ml/kg, 30 and 10 minutes before the intravenous administration of 0.1 ml/kg of a solution of the compound to be studied or of solvent. These peptide injections are subsequently repeated 10, 30, 60 and 120 minutes after the administration of the compound to be studied. According to the duration of action of the compound to be tested, these injections can optionally be extended every 30 minutes without ever exceeding a total of 5 hours.

The variations in the arterial pressure after administration of a given peptide are then evaluated by measuring, at different times, the difference between the maximum effect induced by the peptide agonist and the basal value of the arterial pressure. The results obtained show that NA, A-II, AVP, NPY and ET induce respective increases in the arterial pressure of 45±3, 40±3, 30±2 and 34±4 mmHg and Iso induces an increase in the heart rate of 209±7 beats per minute.

In addition, it is observed that the compounds of the invention antagonize in a dose-dependent fashion the vasoconstrictive effects induced by NA, A-II and AVP. They also antagonize the effects induced by NPY and by ET and the increase in the heart rate induced by Iso. At the highest doses, the maximum inhibition obtained after 15 minutes varies between 40 and 80% and the duration of action is at least greater than or equal to 30 minutes.

V. Toxicity

The toxicity of the compounds of the invention proved to be compatible with their therapeutic use.

The pharmaceutical compositions according to the invention can be presented in any form suitable for administration in human or veterinary therapy. For example, the pharmaceutical compositions of the present invention can be formulated for oral, sublingual, subcutaneous, intramuscular, intravenous, transdermal or rectal administration. As regards the administration unit, the latter can take the form, for example, of a tablet, including a sugar-coated tablet, a capsule, including a hard gelatin capsule, a powder, a suspension, a syrup or granules for oral administration, of a suppository for rectal administration or of a solution or suspension for parenteral administration.

The pharmaceutical compositions of the invention can comprise, per administration unit, for example, from 50 to 500 mg by weight of active ingredient for oral administration, from 50 to 200 mg of active ingredient for rectal administration and from 50 to 150 mg of active ingredient for parenteral administration. Depending upon the administration route chosen, the pharmaceutical or veterinary compositions of the invention will be prepared by combining at least one of the compounds of formula (1) or a pharmaceutically acceptable salt of this compound with an appropriate excipient, it being possible for the latter to be composed, for example, of at least one ingredient selected from the following substances: lactose, starches, talc, magnesium stearate, polyvinylpyrrolidone, alginic acid, colloidal silica, distilled water, benzyl alcohol or sweetening agents. When the compositions are tablets, the latter can be treated so that they exhibit a sustained or delayed activity and that they continually release a predetermined amount of active principle.

The following nonlimiting examples illustrate the preparation of the compounds and compositions of the invention:

EXAMPLE 1

Isopropyl 2-butyl-3-[4-[(E)-3-(dibutylamino)-1-propenyl]benzoyl]-1-benzofuran-5-carboxylate hydrochloride A. Isopropyl 2-butyl-3-[4-(trifluoromethane-sulfonyloxy)benzoyl]-1-benzofuran-5-carboxylate 11.7 g (30.8 mmol) of isopropyl 2-butyl-3-(4-hydroxybenzoyl)-1-benzofuran-5-carboxylate are introduced into 100 ml of dichloromethane comprising 2.67 g (33.8 mmol) of pyridine.

9.54 g (33.8 mmol) of trifluoromethane-sulfonic anhydride in 50 ml of dichloromethane are then added between 0° and 5° C. The reaction medium is stirred at ambient temperature for 1 hour 30 minutes and then is concentrated to dryness. The residue is taken up in diethyl ether and then washed with water, dilute hydrochloric acid, water, a sodium hydrogen-carbonate solution, water and then a sodium chloride solution. The organic phase is concentrated to dryness and the residue is then triturated in heptane. The product is then filtered off through a sintered glass funnel.

11 g of desired compound are obtained in this way.

Yield: 69.6% M.p.: 100–101° C.

B. Isopropyl 2-butyl-3-[4-[(E)-3-(dibutylamino)-1-propenyl]benzoyl]-1-benzofuran-5-carboxylate hydrochloride 4.17 g (8.1 mmol) of compound obtained in the preceding paragraph, 3.73 g (1 equivalent) of (E)-1-tributyltin-3-(dibutylamino)-1-propene, 0.96 g of lithium chloride and 1.08 g of tetrakis(triphenyl-phosphine)palladium are dissolved under argon in 100 ml of dioxane. The mixture is brought to reflux for 3 hours, it is evaporated and the residue is taken up in water. Extraction is carried out with diethyl ether and the organic phase is washed with water and a saturated sodium chloride solution. Purification is then carried out by chromatography on silica (eluent: dichloromethane/methanol/aqueous ammonia 100/3/0.2), which gives 4.95 g (yield: 100%) of desired compound in the basic form.

4.90 g of the basic compound thus obtained are then dissolved in diethyl ether and a solution of hydrogen chloride in diethyl ether is added. Crystallization from diethyl ether is subsequently allowed to take place.

3 g of desired compound are obtained in this way.

Yield: 64% M.p.: 147–149° C.

By using the same process as above, the following compounds were prepared:
Methyl 2-butyl-6-methyl-3-[4-[(E)-3-(dibutylamino)-propyl]benzoyl]-1-benzofuran-5-carboxylate hydrochloride (Example 2)

Yield: 58.4% NMR (nuclear magnetic resonance) spectrum (200 MHz) Solvent: DMSO (dimethyl sulfoxide) at 2.5 ppm DOH at 3.33 ppm δ (ppm): 0.6 to 1; broad unresolved peak; 9H, 3CH$_3$ 1 to 1.9; broad unresolved peak; 12H, 6CH$_2$ 2.6; singlet; 3H, CH$_3$ 2.7; triplet; 2H, CH$_2$ 3; multiplet; 4H, 2CH$_2$N 3.75; singlet; 3H, OCH$_3$ 3.9; multiplet; 2H NCH$_2$ 6.6; split triplet; 1H, CH 7; doublet; 1H, CH 7.4 to 8.1; broad unresolved peak; 6H, aromatic $^1$H 10.8; broad singlet; 1H, NH$^+$

EXAMPLE 3

Isopropyl 2-butyl-3-[4-[(Z)-3-(dibutylamino)-1-propenyl]benzoyl]-1-benzofuran-5-carboxylate oxalate A. Isopropyl 2-butyl-3-[4-[(Z)-3-(dibutylamino)-1-propynyl]benzoyl]-1-benzofuran-5-carboxylate 5 g (9.75 mmol) of isopropyl 2-butyl-3-[4-(trifluoromethanesulfonyloxy)benzoyl]-1-benzofuran-5-carboxylate are introduced under argon into 50 ml of N,N-dimethylformamide and then 1.63 g of 3-(dibutylamino)-1-propyne, 6.72 ml of triethylamine, 0.341 g of dichlorobis(triphenylphosphine)palladium and 0.094 g of cuprous iodide are added. The mixture is heated at approximately 90° C. for 3 hours and is then evaporated, and the residue is taken up in diethyl ether. The organic phase is washed with water and a sodium chloride solution and purification is then carried out by chromatography on silica (eluent: dichloromethane/methanol 99/1).

4.84 g of the desired compound are obtained in this way. Yield: 91%

B. Isopropyl 2-butyl-3-[4-[(Z)-3-(dibutylamino)-1-propenyl]benzoyl]-1-benzofuran-5-carboxylate-oxalate 4.8 g (8.8 mmol) of compound obtained above are introduced into 100 ml of toluene. A spatulafull of animal charcoal is added, the mixture is stirred and is filtered through diatomaceous earth. The filter residue is rinsed with 150 ml of toluene, 0.480 g of Lindlar palladium-on-charcoal is added to this filtrate and then hydrogenation is carried out at 25° C. and at standard pressure.

The progress of the reaction is monitored by thin layer chromatography and 0.480 g portions of palladium-on-charcoal are added until the end of this reaction. The mixture is filtered through diatomaceous earth, the filter residue is rinsed and purification is carried out by chromatography on silica (eluent: dichloromethane/methanol/20% aqueous ammonia: 98/2/0.2), which gives 2.05 g (yield: 48.3%) of desired compound in the free base form. 1.94 g of basic compound thus obtained are then dissolved in 20 ml of methanol, and then a solution of 0.328 g of oxalic acid in 20 ml of methanol is added. The mixture is evaporated and the residue is taken up in diethyl ether. The product is filtered off, washed with diethyl ether and dried under vacuum.

1.649 g of desired compound are obtained in this way. Yield: 73% M.p.: 78–80° C.

By using the same process as that described above, the following compound was prepared:
Isopropyl 2-butyl-6-methyl-3-[4-[(Z)-3-(dibutylamino)-1-propenyl]benzoyl]-1-benzofuran-5-carboxylate hydrochloride (Example 4).

M.p.: 129° C.

EXAMPLE 5

2-Butyl-3-[4-[(Z)-3-(dibutylamino)-1-propenyl]-benzoyl]-1-benzofuran-5-carboxylic acid oxalate 2.26 g of methyl 2-butyl-3-[4-[(Z)-3-(dibutylamino)-1-propenyl]benzoyl]-1-benzofuran-5-carboxylate and 0.360 g (2 equivalents) of sodium hydroxide are introduced into 25 ml of dioxane and then 5 ml of water and 5 ml of methanol are added. The mixture is stirred at ambient temperature for 24 hours and is then evaporated. The residue is taken up in water and acidified to pH=5 to 6 with dilute hydrochloric acid.

Extraction is carried out with ethyl acetate and the extract is washed with a saturated sodium chloride solution. Purification is then carried out by chromatography on silica (eluent: dichloromethane/methanol 100/7), which gives 1.45 g (yield: 66%) of the desired compound in the free base form.

2.25 g of the basic compound thus obtained and 0.414 g of oxalic acid are then introduced into acetone. The mixture is evaporated and crystallization from diethyl ether is allowed to take place.

2.12 g of the desired compound are collected in this way.

Yield: 79.5% M.p.: 89–92° C.

EXAMPLE 6

2-Butyl-3-[4-[(Z)-3-(dibutylamino)-1-propenyl)-benzoyl]-1-benzofuran-5-carboxamide oxalate 6.79 g (13.9 mmol) of 2-butyl-3-[4-(Z)-3-(dibutylamino)-1-propenyl]benzoyl]-1-benzofuran-5-carboxylic acid are introduced into 100 ml of dichloromethane and then 3.13 g (15.2 mmol) of dicyclohexylcarbodiimide and 2.05 g (15.2 mmol) of hydroxybenzotriazole are added. The mixture is stirred at ambient temperature for 0.5 hour, is then cooled to 5° C. and 2.6 ml of 20% aqueous ammonia are added. The mixture is again stirred at ambient temperature for 18 hours and is then cooled. The mixture is filtered through a sintered glass funnel and the filtrate is washed with water, a sodium hydrogencarbonate solution and then with water. The filtrate is dried and concentrated and the residue is purified by chromatography on silica (eluent: dichloromethane/methanol/ammonia 100/3/0.1), which gives 2.92 g (yield: 43%) of desired compound in the basic form.

2.90 g (5.94 mmol) of basic compound thus obtained are subsequently introduced into an amount of methanol necessary to obtain complete dissolution and then 0.535 g (5.9 mmol) of oxalic acid is added. The mixture is concentrated to dryness and the residue is triturated in diethyl ether, filtered off and then dried.

2.36 g of desired compound are collected in this way in the form an amorphous solid.

NMR spectrum (200 MHz) Solvent: DMSO at 2.5 ppm δ (ppm): 0.6 to 0.9; broad unresolved peak; 9H, 3CH$_3$ 1 to 1.8; broad unresolved peak; 12H, 6CH$_2$ 2.75; triplet; 2H, CH$_2$ 2.9; multiplet; 4H, 2NCH$_2$ 3.95; doublet; 2H, NCH$_2$ 6; split triplet; 1H, CH 6.9; doublet; 1H, CH 7.05 to 8.1; broad unresolved peak; 9H, 7 aromatic $^1$H, NH$_2$

EXAMPLE 7

2-Butyl-3-[4-[(Z)-3-(dibutylamino)-1-propenyl]-benzoyl]-N,N-dimethyl-1-benzofuran-5-carboxamide oxalate A. 2-Butyl-3-(4-hydroxybenzoyl)-N,N-dimethyl-3-benzofuran-5-carboxamide 6 g of 2-butyl-3-(4-hydroxybenzoyl)-1-benzofuran-5-carboxylic acid and 10 ml of thionyl chloride are introduced into 300 ml of 1,2-dichloro-ethane. The mixture is brought to reflux for 7 hours and is then concentrated to dryness. This chloride is then dissolved in 100 ml of dichloromethane and the solution is saturated at 5° C. with the necessary amount of dimethylamine in the gas form. The mixture is then stirred at ambient temperature for 72 hours. Washing is carried out with water, dilute hydrochloric acid, water and then a saturated sodium chloride solution. Purification is subsequently carried out by chromatography on silica (eluent: dichloromethane/methanol 97/3).

5.2 g of the desired compound are obtained in this way.

Yield: 80.9% (with respect to the starting 5-carboxylic compound)

B. 2-Butyl-3-[4-(trifluoromethanesulfonyloxy)-benzoyl]-N,N-dimethyl-1-benzofuran-5-carboxamide 5.1 g (14 mmol) of compound obtained in the preceding stage are introduced into 50 ml of dichloromethane, and 2.52 ml of pyridine are added. 5.26 ml (31.3 mmol) of trifluoromethanesulfonic anhydride in 30 ml of dichloromethane are then added at a temperature of less than 10° C. The mixture is stirred at ambient temperature for 4 hours, is concentrated to dryness and the residue is taken up in ethyl acetate. Washing is carried out with water, dilute hydrochloric acid, water, a sodium hydrogencarbonate solution, water and a sodium chloride solution. Purification is then carried out by thin layer chromatography (eluent: dichloromethane/ethyl acetate 95/[lacuna], then 90/10, then 80/20).

5.358 g of desired compound are obtained in this way.

Yield: 76.9%

C. 2-Butyl-3-[4-[3-(dibutylamino)-1-propynyl]-benzoyl]-N,N-dimethyl-1-benzofuran-5-carboxamide 5.338 g (10.73 mmol) of compound obtained in the preceding stage are introduced under argon into 60 ml of N,N-dimethylformamide and then 1.8 g (10.73 mmol) of 3-(dibutylamino)-1-propyne are added. 7.39 ml of triethylamine, 0.376 g of dichlorobis(tri-phenylphosphine) palladium and then 0.104 g of cuprous iodide are subsequently added. The mixture is heated at 90° C. for 4 hours, is cooled and is diluted with water. Extraction is carried out with diethyl ether and the organic phase is washed with water and then with a sodium chloride solution. Purification is subsequently carried out by chromatography on silica (eluent: dichloromethane/methanol 98/2).

3.339 g of desired compound are obtained in this way.

Yield: 60.4%

D. 2-Butyl-3-[4-[(Z)-3-(dibutylamino)-1-propenyl] benzoyl]-N,N-dimethyl-1-benzofuran-5-carboxamide oxalate 3.32 g of compound obtained in the preceding stage are dissolved in 100 ml of toluene, 1.32 g of Lindlar palladium-on-charcoal are then added and hydrogenation is carried out at ambient temperature and at standard pressure. The mixture is filtered through diatomaceous earth and the solvent is evaporated under reduced pressure. The residue is subsequently purified by chromatography on silica (eluent: dichloromethane/methanol/aqueous ammonia 98/2/0.1), which gives 1.105 g (yield: 33.1%) of desired compound in the basic form.

1.095 g (2.12 mmol) of basic compound thus obtained are then introduced into the amount of methanol necessary to obtain complete dissolution and then 0.191 g (2.12 mmol) of oxalic acid is added. The mixture is concentrated to dryness and the residue is triturated in diethyl ether. The product is filtered off and then dried.

1.053 g of desired compound are obtained in this way.

Yield: 81.8% NMR spectrum (200 MHz) Solvent: DMSO at 2.5 ppm δ (ppm): 0.7 to 1.1; broad unresolved peak; 9H, 3CH$_3$ 1.1 to 1.9; broad unresolved peak; 12H, 6CH$_2$ 2.7 to 3.2; broad unresolved peak; 12H, 3CH$_2$, 2NCH$_2$ 4.15; doublet; 2H, NCH$_2$ 6.1; split triplet; 1H, CH 7; doublet; 1H, CH 7.3 to 8; broad unresolved peak; 7H, aromatic $^1$H

EXAMPLE 8

Isopropyl 2-butyl-3-[3-[(Z)-3-(dibutylamino)-1-propenyl]benzoyl]-1-benzofuran-5-carboxylate oxalate A. Methyl 2-butyl-3-(3-methoxybenzoyl)-1-benzofuran-5-carboxylate 14.8 g (63.7 mmol) of methyl 2-butyl-1-benzofuran-5-carboxylate and 21.6 g (127 mmol) of 3-methoxybenzoyl chloride are introduced into 300 ml of 1,2-dichloroethane, 21.6 g (127.4 mmol) of ferric chloride are then added portionwise and the mixture is stirred at ambient temperature for approximately 8 hours. The mixture is poured into a water/ice mixture, the layers are separated by settling and the aqueous layer is extracted with dichloromethane. Washing is carried out with water, a dilute sodium hydrogencarbonate solution and then with water.

20.52 g of desired compound are obtained in this way.
Yield: 87.9%

B. Methyl 2-butyl-3-(3-hydroxybenzoyl)-1-benzofuran-5-carboxylate 21.73 g (59.3 mmol) of compound obtained in the preceding stage are introduced into 500 ml of toluene, and 23.72 g (178 mmol) of aluminum chloride are added. The mixture is heated at 60° C. for 4 hours, is cooled and is separated by settling. The insoluble material present in the toluene is dissolved in tetrahydrofuran, a mixture of water and of ice is added and extraction is carried out with ethyl acetate. The organic extracts are combined and washed several times with water and with a sodium chloride solution. They are dried and concentrated.

22 g of desired compound are obtained in this way in the crude form.

C. 2-Butyl-3-(3-hydroxybenzoyl)-1-benzofuran-5-carboxylic acid 19 g (53.9 mmol) of compound obtained in the preceding stage are introduced into 300 ml of dioxane and then 4.31 g (107.8 mmol) of sodium hydroxide in 150 ml of water are added. The mixture is stirred at ambient temperature for 5 hours and is then concentrated to dryness. The residue is taken up in water and is acidified with dilute hydrochloric acid. Extraction is then carried out with ethyl acetate.

23 g of desired compound are obtained in this way in the crude form.

D. Isopropyl 2-butyl-3-(3-hydroxybenzoyl)-1-benzofuran-5-carboxylate 23.5 g of crude compound obtained in the preceding stage and 5 ml of sulfuric acid are introduced into 500 ml of isopropanol. The mixture is brought to reflux for approximately 12 hours and is concentrated to dryness. The residue is taken up in ethyl acetate and is washed successively with water, a sodium hydrogencarbonate solution, water and a sodium chloride solution. Purification is subsequently carried out by chromatography on silica (eluent: dichloromethane/methanol 99/1, then 98/2).

13.3 g of desired compound are obtained in this way.

E. Isopropyl 2-butyl-3-[3-(trifluoromethanesulfonyloxy)benzoyl]-1-benzofuran-5-carboxylate 10 g (26.3 mmol) of compound obtained in the preceding stage are introduced into 100 ml of dichloro-methane and then 2.33 ml (28.9 mmol) of pyridine are added. 4.87 ml (28.9 mmol) of trifluoromethanesulfonic anhydride in 50 ml of dichloromethane are then added between 5° and 10° C.

The mixture is stirred at ambient temperature for approximately 8 hours and is concentrated to dryness. The residue is taken up in ethyl acetate and is washed with water, dilute hydrochloric acid, a sodium hydrogencarbonate solution, water and finally with a sodium chloride solution.

Purification is subsequently carried out by chromatography on silica (eluent: dichloromethane).

8.31 g of desired compound are obtained in this way.
Yield: 61.6%

F. Isopropyl 2-butyl-3-[3-[3-(dibutylamino)-1-propynyl]benzoyl]-1-benzofuran-5-carboxylate 8.3 g (16.2 mmol) of compound obtained in the preceding stage are introduced under argon into 80 ml of N,N-dimethylformamide and then 2.71 g (16.2 mmol) of 3-dibutylamino-1-propyne, 11.16 ml of triethylamine, 0.566 g of dichlorobis(triphenylphosphine)palladium and 0.156 g of cuprous iodide are added. The mixture is heated at approximately 90° C. for 6 hours. The reaction mixture is poured into water and is then extracted with diethyl ether. Washing is carried out with water and chromatography is carried out on silica (eluent: dichloromethane/methanol 99/1).

5.2 g of desired compound are obtained in this way.
Yield: 60.6%

G. Isopropyl 2-butyl-3-[3-[(Z)-3-(dibutylamino)-1-propenyl]benzoyl]-1-benzofuran-5-carboxylate oxalate 5.2 g (10.1 mmol) of compound obtained in the preceding stage are introduced into toluene and the solution obtained is hydrogenated in the presence of 0.520 g of Lindlar palladium-on-charcoal. The reaction is monitored by thin layer chromatography and 0.520 g fractions of palladium-on-charcoal are added depending on the degree of progression of the reaction. The mixture is filtered through diatomaceous earth and the filtrate is concentrated. Purification is then carried out by chromatography on silica (eluent: dichloro-methane/methanol 97/3), which gives 2.586 g of desired compound in the basic form.

2.56 g (48.1 mmol) of basic compound obtained in the preceding stage are then introduced into the amount of methanol necessary to obtain complete dissolution. 0.433 g (48.1 mmol) of oxalic acid is subsequently added and the mixture is concentrated to dryness. The residue is triturated in diethyl ether and the product is filtered off and dried.

2.516 g of desired compound are collected in this way.
M.p.: 76–78° C.

EXAMPLE 9

2-Butyl-3-[4-[(Z)-3-(dibutylamino-1-propenyl] benzoyl-5-(1H-tetrazol-5-yl)-1-benzofuran oxalate 3.32 g (7.06 mmol) of 2-butyl-3-[4-[(Z)-3-(dibutylamino)-1-propenyl]benzoyl]-1-benzofuran-5-carbonitrile are introduced into 70 ml of toluene and then 3 g (8.9 mmol) of tributyltin azide are added. The mixture is brought to reflux for 3 and a half days and is then concentrated to dryness. Purification is subsequently carried out by chromatography on silica (eluent: dichloromethane/methanol 90/10), which gives 3.105 g of desired compound in the basic form.

3.034 g (5.91 mmol) of basic compound thus obtained are subsequently introduced into the amount of methanol necessary to obtain dissolution and then 0.532 g (5.91 mmol) of oxalic acid is added. The mixture is concentrated, the residue is triturated in diethyl ether and the product is filtered off.

2.99 g of desired compound are obtained in this way.
M.p.: 173–174° C.

EXAMPLE 10

Isopropyl 2-butyl-3-[4-[(Z)-3-butylamino-1-propenyl]benzoyl]-1-benzofuran-5-carboxylate hydrochloride

A. Isopropyl 3-(4-[3-[(tert-butoxycarbonyl)-(butyl)amino]-1-propynyl]benzoyl)-2-butyl-1-benzofuran-5-carboxylate 11.04 g (22 mmol) of isopropyl 2-butyl-3-[4-(trifluoromethanesulfonyloxy)benzoyl]-1-benzofuran-5- carboxylate, 4.55 g (22 mmol) of 3-(N-butyl-N-tert-butoxycarbonyl)amino-1-propyne, 0.875 g of dichlorobis-(triphenylphosphine)palladium and 0.312 g of cuprous iodide are mixed in 180 ml of N,N-dimethylformamide comprising 18 ml of triethylamine. The mixture is heated at 90° C. for 3 hours under argon and then poured into a water/ice mixture. Extraction is carried out with diethyl ether and then washing is carried out with water and a saturated sodium chloride solution. Purification is subsequently carried out by chromatography on silica (eluent: dichloromethane/ethyl acetate 100/2).

9.73 g of desired compound are obtained in this way.

Yield: 77%

B. Isopropyl 2-butyl-3-[4-[3-butylamino-1-propynyl]benzoyl]-1-benzofuran-5-carboxylate hydrochloride 0.940 g of compound obtained in the preceding stage is introduced into 20 ml of a 3M hydrochloric acid/ethyl acetate solution and the mixture is stirred at ambient temperature for 2 hours. It is evaporated and the residue is crystallized from diethyl ether.

0.706 g of desired compound is collected in this way.

Yield: 84.5% M.p.: 166–167° C.

C. Isopropyl 2-butyl-3-[4-[(Z)-3-butylamino-1-propenyl]benzoyl]-1-benzofuran-5-carboxylate hydrochloride 0.680 g of compound obtained in the preceding stage is introduced into 20 ml of ethanol and hydrogenation is carried out in the presence of 0.090 g of Lindlar palladium-on-charcoal. 0.120, 0.160 and 0.200 g of palladium-on-charcoal are then successively added, depending on the degree of progression of the reaction. The mixture is subsequently filtered through diatomaceous earths and purification is carried out by chromatography on silica (eluent: dichloromethane/methanol/aqueous ammonia 100/3/0.2), which gives 0.340 g (yield: 67%) of desired compound in the basic form.

0.320 g of basic compound thus obtained is then introduced into diethyl ether, and a solution of hydrogen chloride in diethyl ether is added. The mixture is evaporated and the residue is crystallized from diethyl ether.

0.310 g of desired compound is collected in this way.

Yield: 89% M.p.: 175–176° C.

EXAMPLE 33

2-(Dimethylamino)ethyl 2-butyl-3-(4-[(E)-3-(dibutyl-amino)-1-propenyl]benzoyl)-1-benzofuran-5-carboxylate oxalate

A. 2-(Dimethylamino)ethyl 2-butyl-3-(4-hydroxybenzoyl)-benzofuran-5]-carboxylate 11.63 g (0.0344 mol) of 2-butyl-3-(4-hydroxy-benzoyl)benzofuran-5-carboxylic acid, 250 ml of N,N-dimethylformamide and 5.58 g (0.0344 mol) of carbonyldiimidazole are mixed. The mixture is heated at 40° C. for 2 hours and then 5.23 g (0.0344 mol) of DBU (1,8-diazabicyclo[5.4.0]undec-7-ene) and 6.13 g (0.0687 mol) of 2-(dimethylamino)ethanol are added. The mixture is stirred while heating at 40° C. for 18 hours. It is concentrated to dryness, the residue is then taken up in ethyl acetate and the solution is washed with water. Purification is carried out by chromatography on silica (eluent: 95/5 dichloromethane/methanol).

9.35 g of the desired compound are obtained in this way.

Yield: 66.4%

B. 2-(Dimethylamino)ethyl 2-butyl-3-[4-(trifluoro-methanesulfonyloxy)benzoyl]benzofuran-5-carboxylate 10.49 g (0.0256 mol) of the compound obtained in the preceding stage A, 150 ml of EtCl$_2$ (1,2-dichloro-ethane) and (4.46) g, i.e. (0.056) mol, of pyridine are mixed. (15.88) g, i.e. (0.056) mol, of triflic anhydride dissolved in 300 ml of dichloromethane are added to this mixture at a temperature of less than 10° C. The mixture is stirred at ambient temperature for 5 days, is concentrated to dryness and then the residue is taken up in water NaHCO$_3$ is subsequently added until a basic pH is reached. Extraction is carried out with ethyl acetate and the extract is washed with water. Purification is carried out by chromatography on silica (eluent: 90/10 dichloromethane/methanol).

3.52 g of the desired compound are obtained in this way.

Yield: 25.4%

C. 2-(Dimethylamino)ethyl 2-butyl-3-(4-[(E)-3-(dibutyl-amino)-1-propenyl]benzoyl)-1-benzofuran-5-carboxylate 4.97 g (0.00918 mol) of the compound obtained in the preceding stage B, 150 ml of dioxane, 4.23 g (0.00918 mol) of (E)-1-tributyltin-3-(dibutylamino)-1-propene, 1.084 g of lithium chloride and 1.224 g of tetrakis(triphenylphosphine) palladium are mixed. The mixture is brought to reflux for 5 hours. It is concentrated to dryness and the residue is taken up in ethyl acetate and then washed with water. Purification is carried out by chromatography on silica (eluent: 90/10 dichloromethane/methanol and then 95/5/0.2 dichloromethane/methanol/NH$_4$OH.

0.84 g of the desired compound is obtained in this way.

Yield: 16.3%.

D. 2-(Dimethylamino)ethyl 2-butyl-3-(4-[(E)-3-(dibutyl-amino)-1-propenyl]benzoyl)-1-benzofuran-5-carboxylate oxalate 835 mg (0.00149 mol) of the compound obtained in the preceding stage C, an amount of methanol sufficient for complete dissolution and 268 mg (0.00298 mol) of oxalic acid are mixed. The mixture is subsequently concentrated to dryness and the residue is taken up in ether. The product is filtered off and dried.

890 mg of the desired compound are obtained in this way.

Yield: 80.6%

By using the processes described in the preceding examples, the compound lists below were prepared:

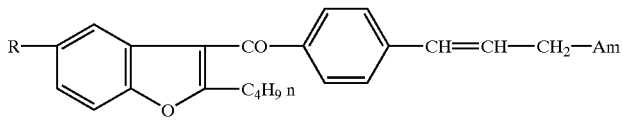

| R | Am | Characteristics | Example |
|---|---|---|---|
| H₃CO₂C— | —N(C₄H₉)₂ | (Z) Isomer<br>Oxalate<br>M.p.: 128° C. | 11 |
| H₃CO₂C— | (N-piperidinyl) | (Z) Isomer<br>Hydrochloride<br>White solid<br>Amorphous | 12 |
| H₃CO₂C— | N(C₂H₅)(cyclohexyl) | (Z) Isomer<br>Hydrochloride<br>Amorphous solid | 13 |
| H₃CO₂C— | 4,4-dimethylpiperidinyl | (Z) Isomer<br>Hydrochloride<br>White solid<br>M.p.: 156° C. | 14 |
| i-H₇C₃O₂C— | —N(C₂H₅)₂ | (Z) Isomer<br>Oxalate<br>M.p.: 148° C. | 15 |
| i-H₇C₃O₂C— | (N-piperidinyl) | (Z) Isomer<br>Hydrochloride | 16 |
| i-H₇C₃O₂C— | N(C₂H₅)(cyclohexyl) | (Z) Isomer<br>Hydrochloride<br>Amorphous powder | 17 |
| i-H₇C₃O₂C— | 3,3-dimethylpiperidinyl | (Z) Isomer<br>Oxalate<br>White solid<br>M.p.: 148° C. | 18 |
| cyclopentyl-O₂C— | —N(C₄H₉)₂ | (Z) Isomer<br>Oxalate<br>M.p.: 77° C. | 19 |
| NC— | —N(C₄H₉)₂ | (Z) Isomer<br>Oxalate<br>M.p.: 126° C. | 20 |
| H₃CO₂C— | —N(C₄H₉)₂ | (E) Isomer<br>Hydrochloride<br>M.p.: 88° C. | 21 |
| HO₂C— | —N(C₄H₉)₂ | (E) Isomer<br>Oxalate<br>Solid<br>M.p.: 87–90° C. | 22 |
| i-H₇C₃O₂C— | —(CH₂)N(C₄H₉)₂ | (E) Isomer<br>Oxalate<br>Solid<br>M.p.: 102–104° C. | 23 |
| n-C₁₃H₆O₂C— | —N(C₄H₉)₂ | (E) Isomer<br>Oxalate<br>Solid<br>M.p.: 97–100° C. | 24 |

-continued

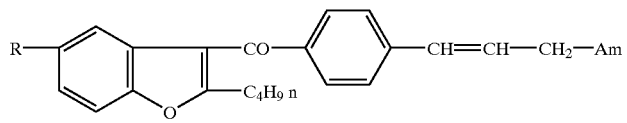

| R | Am | Characteristics | Example |
|---|---|---|---|
| i-H$_7$C$_3$O$_2$C— | ![piperidine N-methyl] N-methylpiperidine | (E) Isomer<br>Oxalate<br>Solid<br>M.p.: 175° C. | 25 |
| i-H$_7$C$_3$O$_2$C— | —N(CH$_2$CH$_2$CH(CH$_3$)$_2$)$_2$ with N-methyl | (E) Isomer<br>Oxalate<br>Solid | 26 |
| i-H$_7$C$_3$O$_2$C— | 1-methyl-3,5-diethylpiperidine | (E) Isomer<br>Oxalate<br>Solid | 27 |
| cyclohexyl-O$_2$C-CH$_2$— | —N(C$_4$H$_9$)$_2$ | (E) Isomer<br>Oxalate<br>White solid<br>M.p.: 139–142° C. | 28 |
| i-H$_7$C$_3$O$_2$C— | —N(C$_2$H$_5$)$_2$ | (E) Isomer<br>Oxalate<br>White solid<br>M.p.: 112° C. | 29 |
| i-H$_7$C$_3$O$_2$C— | N-ethyl-N-methyl-cyclohexylamine | (E) Isomer<br>Oxalate<br>Amorphous | 30 |
| i-H$_7$C$_3$O$_2$C— | —NH(C$_4$H$_9$) | (E) Isomer<br>Oxalate<br>Amorphous | 31 |
| i-H$_7$C$_3$O$_2$C— | N-methyl-N-benzyl-(3-propyl) with CH$_3$ | (E) Isomer<br>Oxalate<br>Amorphous | 32 |
| (CH$_3$)$_2$N(CH$_2$)$_2$O$_2$C— | —NH(C$_4$H$_9$) | (E) Isomer | 33 |

The compounds listed below were also prepared.

| Compound | Characteristics | Example |
|---|---|---|
| [structure] | Hydrochloride<br>Solid<br>M.p.: 153–154° C. | 34 |
| [structure] | | 35 |
| [structure] | Hydrochloride<br>Solid<br>M.p.: 166–167° C. | 36 |
| [structure] | Oxalate<br>Amorphous | 37 |
| [structure] | (E) Isomer<br>Hydrochloride<br>White solid<br>M.p.: 110–114° C. | 38 |

-continued
| Compound | Characteristics | Example |
|---|---|---|
| 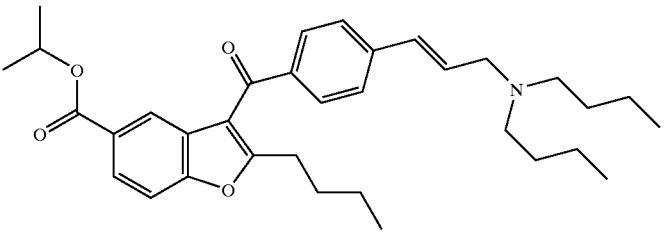 | (E) Isomer<br>Oxalate<br>Solid<br>M.p.: 112° C. | 39 |
| 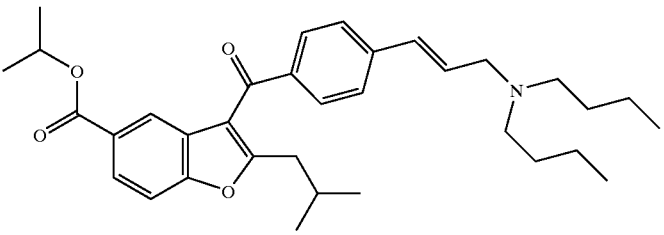 | (E) Isomer<br>Hydrochloride<br>White solid<br>M.p.: 147–150° C. | 40 |
| 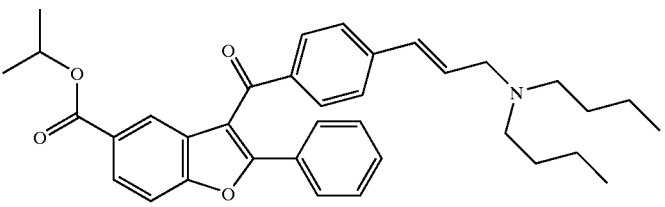 | (E) Isomer | 41 |
| 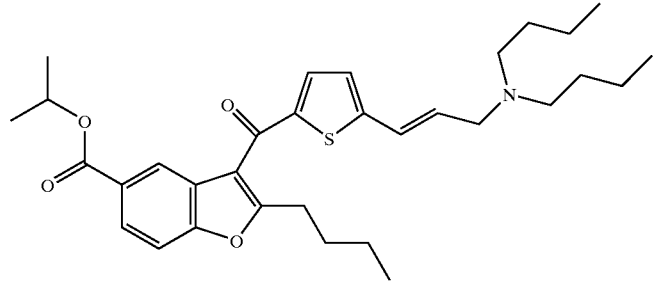 | (E) Isomer | 42 |
| 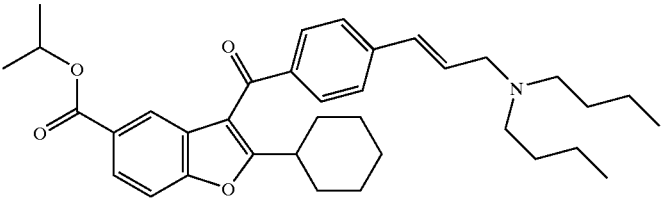 | (E) Isomer<br>Hydrochloride<br>Solid<br>M.p.: 171–173° C. | 43 |
| 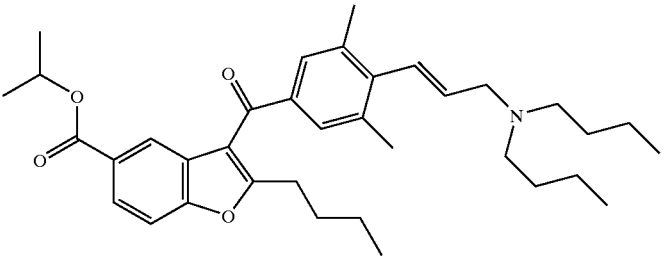 | (E) Isomer<br>Oxalate<br>Powder<br>M.p.: 110–115° C. | 44 |

| Compound | Characteristics | Example |
|----------|-----------------|---------|
| | (E) Isomer | 45 |
| | (E) Isomer<br>Oxalate<br>Amorphous | 46 |
| | (E) Isomer<br>Oxalate<br>Amorphous | 47 |
| | (E) Isomer<br>Oxalate<br>Amorphous | 48 |
| | (E) Isomer<br>Oxalate<br>Amorphous | 49 |
| | (E) Isomer<br>Hydrochloride<br>Solid<br>M.p.: 189–191° C. | 50 |

| Compound | Characteristics | Example |
|---|---|---|
| (structure) | (E) Isomer<br>Oxalate<br>Solid<br>M.p.: 91–93° C. | 51 |
| (structure) | (E) Isomer<br>Oxalate<br>White solid<br>M.p.: 120° C. | 52 |

NMR Spectra at 200 MHz

EXAMPLE 12

Solvent: DMSO at 2.5 ppm δ (ppm): 0.85; triplet; 3H, CH$_3$ 1.1 to 2; broad unresolved peak; 10H, 5CH$_2$ 2.6 to 3; broad unresolved peak; 6H, CH$_2$, 2NCH$_2$ 3.85; singlet; 3H, OCH$_3$ 4.1; multiplet; 2H, NCH$_2$ 6.2; split triplet; 1H, CH 7; doublet; 1H, CH 7.4 to 8.2; broad unresolved peak; 7H, aromatic $^1$H 10.8; broad singlet; 1H, NH$^+$

EXAMPLE 13

Solvent: DMSO at 2.5 ppm δ (ppm): 0.75; triplet; 3H, CH$_3$ 0.9 to 2.1; broad unresolved peak; 15H, CH$_3$, 7CH$_2$ 2.75; triplet; 2H, CH$_2$ 2.8 to 3.5; broad unresolved peak; 3H, NCH$_2$, NCH 3.8; singlet; 3H, OCH$_3$ 4; multiplet; 2H, NCH$_2$ 6.15; split triplet; 1H, CH 6.95; doublet; 1H, CH 7.35 to 8.15; broad unresolved peak; 7H, aromatic $^1$H 10.4; broad singlet; 1H, NH$^+$

EXAMPLE 16

Solvent: DMSO at 2.5 ppm δ (ppm): 0.7; triplet; 3H, CH$_3$ 1.0 to 2; broad unresolved peak; 16H, 2CH$_3$, 5CH$_2$ 2.55 to 3.5; broad unresolved peak; 6H, CH$_2$, 2NCH$_2$ 3.95; multiplet; 2H, CH$_2$N 5; heptet; 1H, OCH 6.05; split triplet; 1H, CH 6.9; doublet; 1H, CH 7.3 to 8; broad unresolved peak; 7H, aromatic $^1$H 10.6; broad singlet; 1H, NH$^+$

EXAMPLE 17

Solvent: DMSO at 2.5 ppm δ (ppm): 0.7; triplet; 3H, CH$_3$ 0.85 to 2.1; broad unresolved peak; 23H, 3CH$_3$, 7CH$_2$ 2.7; triplet; 2H, CH$_2$ 2.8 to 3.3; broad unresolved peak; 3H, NCH$_2$, NCH 4; multiplet; 2H, NCH$_2$ 5.15; heptet; 1H, OCH 6.15; split triplet; 1H, CH 6.9; doublet; 1H, CH 7.3 to 8; broad unresolved peak; 7H, aromatic $^1$H 10.7; broad singlet; 1H, NH$^+$

EXAMPLE 30

Solvent: DMSO δ (ppm): 6.4–8.2 (broad unresolved peak, 9H); 5.09 (quintet, 1H); 3.0–4.2 (broad unresolved peak, 5H); 2.80 (triplet, 2H); 1.0–2.3 (broad unresolved peak, 23H); 0.78 (triplet, 3H)

EXAMPLE 37

Solvent: DMSO δ (ppm): 7.4–8.4 (broad unresolved peak, 7H); 5.12 (quintet, 1H); 3.69 (singlet, 2H); 2.4–2.7 (broad unresolved peak, 2H); 2.78 (triplet, 4H); 0.6–1.7 (broad unresolved peak, 27H)

EXAMPLE 46

Solvent: DMSO δ (ppm): 6.2–8.2 (broad unresolved peak, 9H); 5.09 (quintet, 1H); 3.69 broad doublet, 2H); 3.04 (broad split doublet, 4H): 2.76 (triplet, 2H); 0.6–1.9 (broad unresolved peak, 27H)

EXAMPLE 48

Solvent: DMSO δ (ppm): 6.5–8.0 (broad unresolved peak, 9H); 5.08 (quintet, 1H); 3.89 broad doublet, 2H); 3.21 (quintet, 1H); 3.03 (broad split doublet, 4H): 1.2–1.8 (broad unresolved peak, 20H); 0.90 (triplet, 6H)

EXAMPLE 49

Solvent: DMSO δ (ppm): 6.3–8.0 (broad unresolved peak, 9H); 4.60 (quintet, 1H); 3.83 broad doublet, 2H); 2.96 (broad split doublet, 4H): 2.73 (triplet, 2H); 0.6–1.8 (broad unresolved peak, 27H)

EXAMPLE 22

A capsule was prepared, according to known pharmaceutical techniques, comprising the following ingredients:

| Ingredient | mg |
|---|---|
| Compound of the invention | 100.0 |
| Starch | 99.5 |
| Colloidal silica | 0.5 |

What is claimed is:

1. Benzofuran derivatives of general formula:

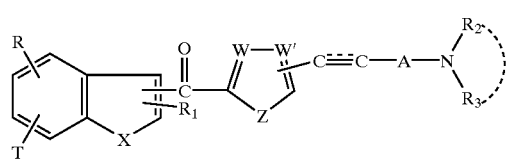

and their pharmaceutically acceptable salts, in which:

represents the —CH=CH— group or the

group,

A represents a linear or branched $C_1$–$C_3$ alkylene group,

T represents hydrogen or a $C_1$–$C_4$ alkyl radical,

R represents:
  the cyano, hydroxymethyl, formyl or tetrazolyl group,
  an ester group of general formula:

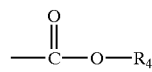

in which $R_4$ represents a $C_1$–$C_6$ alkyl or $C_3$–$C_6$ cycloalkyl group,
a carboxyl group of general formula:

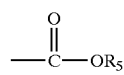

in which $R_5$ represents hydrogen or an alkali metal atom,
an amide group of general formula:

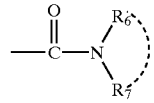

in which $R_6$ and $R_7$, which are identical or different, represent hydrogen or a linear or branched $C_1$–$C_4$ alkyl radical or $R_6$ and $R_7$, when they are taken together, represent a $C_2$–$C_6$ alkylene chain, a group of general formula:

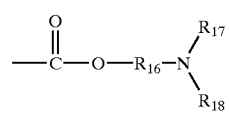

in which $R_{16}$, $R_{17}$ and $R_{18}$, which are identical or different, represent a linear or branched
$C_1$–$C_4$ alkylene group, $R_1$ represents hydrogen, a linear or branched $C_1$–$C_6$ alkyl group, a $C_3$–$C_6$ cycloalkyl group or a phenyl group, $R_2$ and $R_3$, which are identical or different, represent hydrogen, a linear or branched $C_1$–$C_6$ alkyl group or a $C_3$–$C_6$ cycloalkyl group, W, W' and Z are such that:
  when W represents CH and W' represents C—$R_8$, Z represents —CH=C—$R_9$, $R_8$ and $R_9$ being identical or different and representing hydrogen, a halogen atom, a $C_1$–$C_4$ alkyl radical, or a $C_1$–$C_4$ alkoxy radical, X represents —O—, these benzofuran derivatives being in the form of individual isomers or of mixtures of the latter.

2. Benzofuran derivatives according to claim 1 wherein

represents the CH=CH— group.

3. Benzofuran derivatives according to claim 1 wherein R represents the isopropoxycarbonyl group.

4. Benzofuran derivatives according to claim 3 wherein $R_1$ and/or $R_2$ and/or $R_3$ represent the n-butyl group.

5. Benzofuran derivatives according to claim 4 in which:

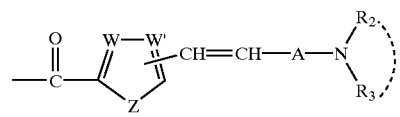

represents the benzoyl group substituted in the 4-position by a

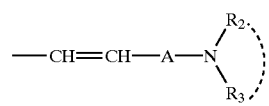

group.

6. Benzofuran derivatives according to claim 5 wherein $R_1$ represents the n-butyl group, A represents the methylene group and $R_2$ and $R_3$, which are identical, represent the n-butyl group.

7. Benzofuran derivatives according to claim 6 wherein they are in the form of isomers with the E configuration.

8. Benzofuran derivatives according to claim 6 wherein they are in the form of isomers with the Z configuration.

9. Isopropyl 2-butyl-3-[4-[(E)-3-(dibutylamino)-1propenyl]benzoyl]-1-benzofuran-5-carboxylate and its pharmaceutically acceptable salts.

10. Isopropyl 2-butyl-3-[4-[(Z)-3-(dibutylamino)-1-propenyl]benzoyl]1-benzofuran-5-carboxylate and its pharmaceutically acceptable salts.

11. Benzofuran derivatives according to claim 1 in which the pharmaceutically acceptable salt is chosen from the maleate, fumarate, methanesulfonate, benzoate, ascorbate, pamoate, succinate, hexamate, bismethylenesalicylate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophyllineacetate, and the salts formed from an amino acid.

12. Benzofuran derivatives according to claim 1 in which the pharmaceutically acceptable salt is chosen from the hydrochloride, hydrobromide, sulfate, sulfamate, phosphate and nitrate.

13. Isopropyl 2-butyl-3-[4-[(E)-3-(dibutylamino)-1-propenyl]benzoyl]-1-benzofuran-5-carboxylate hydrochloride.

14. A process for the preparation of the benzofuran derivatives according to claim 1 in which R represents the cyano group, the formyl group, a group (a) or a group (c), these derivatives being in the form of isomers with the E configuration, wherein a compound of general formula:

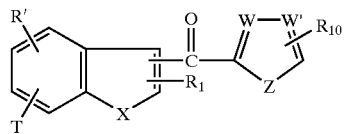

(2)

in which R' represents the cyano group, the formyl group, a group (a) or a group (c), $R_{10}$ represents a halogen atom or the trifluoromethanesulfonyloxy group and R, T, X, W, W' and Z have the same meaning as claim 1, is reacted with an organotin derivative with the E configuration corresponding to the general formula:

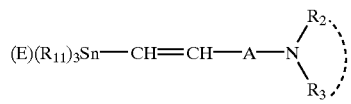

(3)

in which A, $R_2$ and $R_3$ have the same meaning as in claim 1 and $R_{11}$ represents a $C_1$–$C_4$ alkyl radical, after protection of the amine functional group when $R_2$ and/or $R_3$ represent hydrogen, this reaction being carried out in the presence of lithium chloride and of an organopalladium derivative, and then, if necessary, the compound thus formed is deprotected, which gives the desired compounds in the free base form, which can be reacted, if necessary, with an organic or inorganic acid to form a pharmaceutically acceptable salt.

15. A process for the preparation of the benzofuran derivatives according to claim 1 in which R represents the cyano group, the formyl group, a group (a) or a group (c), these derivatives being in the form of isomers with the Z configuration, wherein an alkynyl compound of general formula

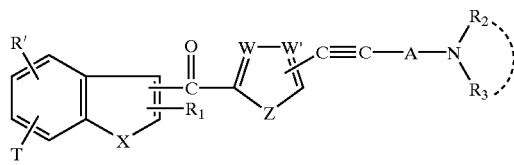

(4)

in which R' represents the cyano group, the formyl group, a group (a) or a group (c) and A, $R_1$, $R_2$, $R_3$, T, W, W', X and Z have the same meaning as in claim 1, is hydrogenated, this reaction being carried out in the presence of an appropriate catalyst, which gives the desired compounds in the free base form, which can be reacted, if necessary, with an organic or inorganic acid to form a pharmaceutically acceptable salt.

16. A process for the preparation of benzofuran derivatives according to claim 1 in which R represents a group (b), wherein a compound of general formula:

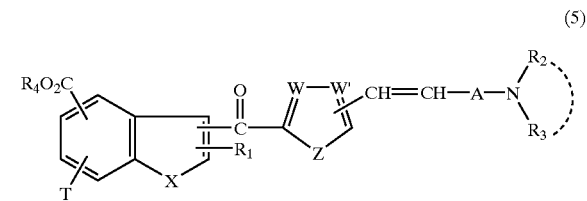

(5)

in which A, $R_1$, $R_2$, $R_3$, $R_4$, T, W, W' and Z have the same meaning as in claim 1, is saponified in the presence of an alkali metal hydroxide, which gives, in the free base form, the desired compounds of formula (1) in which $R_5$ represents an alkali metal atom, which compounds are treated, if necessary, with a strong acid, which gives, in the free base form, the desired compounds of formula (1) in which $R_5$ represents hydrogen, it being possible for the free base thus formed to be treated, if necessary, with an appropriate organic or inorganic acid to obtain a pharmaceutically acceptable salt.

17. A process for the preparation of benzofuran derivatives according to claim 1 in which R represents the hydroxymethyl group, wherein a ketal of general formula:

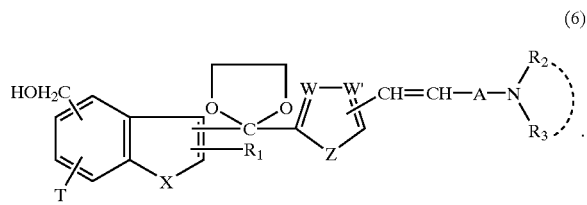

(6)

in which A, $R_1$, $R_2$, $R_3$, T, X, W, W' and Z have the same meaning as in claim 1, is deprotected, this reaction being carried out by means of pyridine p-toluenesulfonate, which gives the derived compounds in the free base form, which can be reacted, if necessary, with an organic or inorganic acid to form a pharmaceutically acceptable salt.

18. A process for the preparation of benzofuran derivatives according to claim 1 in which R represents a group (c) in which $R_6$ and $R_7$ are identical and each represent hydrogen, wherein a compound of general formula:

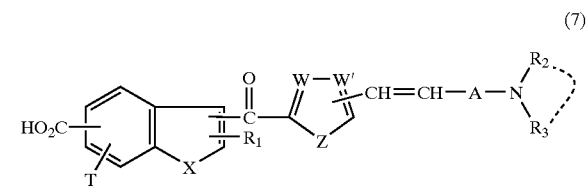

(7)

in which A, $R_1$, $R_2$, $R_3$, T, W, W', X and Z have the same meaning as in claim 1, is reacted by means of dicyclohexylcarbodiimide in the presence of hydroxybenzotriazole and of ammonia, which gives the desired compounds in the free base form, which can be reacted, if necessary, with an organic or inorganic acid to form a pharmaceutically acceptable salt.

19. A process for the preparation of benzofuran derivatives according to claim 1 in which R represents a group (C) in which $R_6$ and $R_7$ each represent hydrogen, wherein a compound of general formula:

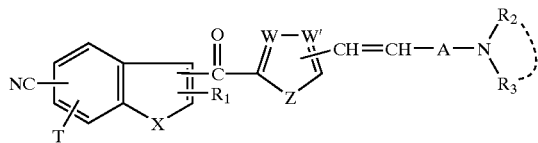

(8)

in which A, $R_1$, $R_2$, $R_3$, T, W, W', X and Z have the same meaning as in claim 1, is hydrolyzed in the presence of a strong acid, which gives the desired compounds in the free base form, which can be reacted, if necessary, with an organic or inorganic acid to form a pharmaceutically acceptable salt.

20. A process for the preparation of benzofuran derivatives according to claim 1 in which R represents the tetrazolyl group, wherein a compound of general formula:

(8)

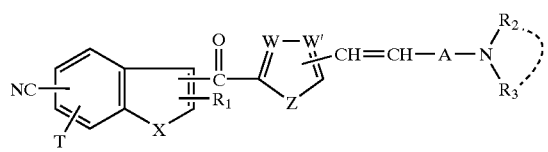

in which A, $R_1$, $R_2$, $R_3$, T, W, W', X and Z have the same meaning as in claim 1, is reacted with a [tri($C_1$–$C_4$ alkyl)] azidotin, which gives the desired compounds in the free base form, which can be reacted, if necessary, with an organic or inorganic acid to form a pharmaceutically acceptable salt.

21. A process for the preparation of benzofuran derivatives according to claim 14, wherein the protection of the amine functional group is carried out by means of a t-butoxycarbonyl anhydride and the deprotection by treatment in an acidic medium.

22. A pharmaceutical or veterinary composition comprising as active principle, at least one benzofuran derivative, or a pharmaceutically acceptable salt of the latter, according to claim 1 in combination with an appropriate excipient or pharmaceutical vehicle. complicated or not complicated by cardiac insufficiency, or for the prevention of postinfarction mortality.

23. A pharmaceutical or veterinary composition according to claim 22 wherein it comprises from 50 to 500 mg of active principle.

24. A method for the treatment of pathological syndromes of the cardiovascular system which comprises administering to a patient in need of such treatment an effective amount of a compound according to claim 1.

25. Benzofuran derivatives according to claim 2 wherein R represents the isopropoxycarbonyl group.

26. Benzofuran derivatives according to claim 1 wherein $R_1$ and/or $R_2$ and/or $R_3$ represent the n-butyl group.

27. Benzofuran derivatives according to claim 2 wherein $R_1$ and/or $R_2$ and/or $R_3$ represent the n-butyl group.

28. Benzofuran derivatives according to claim 1 in which:

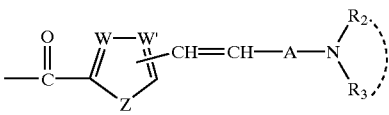

represents the benzoyl group substituted in the 4-position by a

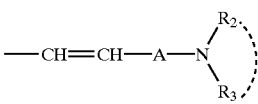

29. Benzofuran derivatives according to claim 2 in which:

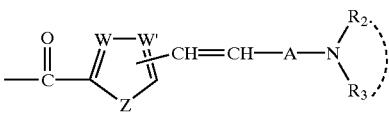

represents the benzoyl group substituted in the 4-position by a

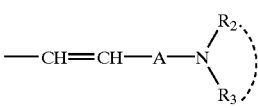

group.

30. Benzofuran derivatives according to claim 1 wherein $R_1$ represents the n-butyl group, A represents the methylene group and $R_2$ and $R_3$, which are identical, represent the n-butyl group.

31. Benzofuran derivatives according to claim 2 wherein $R_1$ represents the n-butyl group, A represents the methylene group and $R_2$ and $R_3$, which are identical, represent the n-butyl group.

32. Benzofuran derivatives according to claim 1 wherein they are in the form of isomers with the E configuration.

33. Benzofuran derivatives according to claim 2 wherein they are in the form of isomers with the E configuration.

34. Benzofuran derivatives according to claim 1 wherein they are in the form of isomers with the Z configuration.

35. Benzofuran derivatives according to claim 2 wherein they are in the form of isomers with the Z Configuration.

36. Benzofuran derivatives according to claim 2 in which the pharmaceutically acceptable salt is chosen from the maleate, fumarate, methanesulfonate, benzoate, ascorbate, pamoate, succinate, hexamate, bismethylenesalicylate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophyllineacetate, and the salts formed from an amino acid.

37. Benzofuran Benzofuran or benzothiophene derivatives according to claim 11 in which the pharmaceutically acceptable salt is chosen from the maleate, fumarate, methanesulfonate, benzoate, ascorbate, pamoate, succinate, hexamate, bismethylenesalicylate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophyllineacetate, and the salts formed from an amino acid.

38. Benzofuran derivatives according to claim 10 which the pharmaceutically acceptable salt is chosen from the maleate, fumarate, methanesulfonate, benzoate, ascorbate, pamoate, succinate, hexamate, bismethylenesalicylate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophyllineacetate, and the salts formed from an amino acid.

39. Benzofuran derivatives according to claim 2 in which the pharmaceutically acceptable salt is chosen from the hydrochloride, hydrobromide, sulfate, sulfamate, phosphate and nitrate.

40. Benzofuran derivatives according to claim 9 in which the pharmaceutically acceptable salt is chosen from the hydrochloride, hydrobromide, sulfate, sulfamate, phosphate and nitrate.

41. Benzofuran derivatives according to claim 10 in which the pharmaceutically acceptable salt is chosen from the hydrochloride, hydrobromide, sulfate, sulfamate, phosphate and nitrate.

42. A benzofuran derivative according to claim 11 wherein the salts formed from an amino acid are the lysine or histidine salt.

43. A benzofuran derivative according to claim 37 wherein the salts formed from an amino acid are the lysine or histidine salt.

44. A benzofuran derivative according to claim 38 wherein the salts formed from an amino acid are the lysine or histidine salt.

45. A pharmaceutical or veterinary composition comprising as active principle, at least one benzofuran derivative, or a pharmaceutically acceptable salt of the latter, according to claim 2 in combination with an appropriate excipient or pharmaceutical vehicle.

46. A pharmaceutical or veterinary composition comprising as active principle, at least one benzofuran derivative, or a pharmaceutically acceptable salt of the latter, according to claim 3 in combination with an appropriate excipient or pharmaceutical vehicle.

47. A pharmaceutical or veterinary composition comprising as active principle, at least one benzofuran derivative, or a pharmaceutically acceptable salt of the latter, according to claim 4 in combination with an appropriate excipient or pharmaceutical vehicle.

48. A pharmaceutical or veterinary composition comprising as active principle, at least one benzofuran derivative, or a pharmaceutically acceptable salt of the latter, according to claim 5 in combination with an appropriate excipient or pharmaceutical vehicle.

49. A pharmaceutical or veterinary composition comprising as active principle, at least one benzofuran derivative, or a pharmaceutically acceptable salt of the latter, according to claim 6 in combination with an appropriate excipient or pharmaceutical vehicle.

50. A pharmaceutical or veterinary composition comprising as active principle, at least one benzofuran derivative, or a pharmaceutically acceptable salt of the latter, according to claim 7 in combination with an appropriate excipient or pharmaceutical vehicle.

51. A pharmaceutical or veterinary composition comprising as active principle, at least one benzofuran derivative, or a pharmaceutically acceptable salt of the latter, according to claim 8 in combination with an appropriate excipient or pharmaceutical vehicle.

52. A pharmaceutical or veterinary composition comprising as active principle, at least one benzofuran derivative, or a pharmaceutically acceptable salt of the latter, according to claim 9 in combination with an appropriate excipient or pharmaceutical vehicle.

53. A pharmaceutical or veterinary composition comprising as active principle, at least one benzofuran derivative, or a pharmaceutically acceptable salt of the latter, according to claim 10 in combination with an appropriate excipient or pharmaceutical vehicle.

54. A pharmaceutical or veterinary composition comprising as active principle, at least one benzofuran derivative, or a pharmaceutically acceptable salt of the latter, according to claim 11 in combination with an appropriate excipient or pharmaceutical vehicle.

55. A pharmaceutical or veterinary composition comprising as active principle, at least one benzofuran derivative, or a pharmaceutically acceptable salt of the latter, according to claim 12 in combination with an appropriate excipient or pharmaceutical vehicle.

56. A pharmaceutical or veterinary composition comprising as active principle, at least one benzofuran derivative, or a pharmaceutically acceptable salt of the latter, according to claim 13 in combination with an appropriate excipient or pharmaceutical vehicle.

57. A pharmaceutical or veterinary composition comprising as active principle, at least one benzofuran derivative, or a pharmaceutically acceptable salt of the latter, according to claim 25 in combination with an appropriate excipient or pharmaceutical vehicle.

58. A pharmaceutical or veterinary composition comprising as active principle, at least one benzofuran derivative, or a pharmaceutically acceptable salt of the latter, according to claim 26 in combination with an appropriate excipient or pharmaceutical vehicle.

59. A pharmaceutical or veterinary composition comprising as active principle, at least one benzofuran derivative, or a pharmaceutically acceptable salt of the latter, according to claim 27 in combination with an appropriate excipient or pharmaceutical vehicle.

60. A pharmaceutical or veterinary composition comprising as active principle, at least one benzofuran derivative, or a pharmaceutically acceptable salt of the latter, according to claim 28 in combination with an appropriate excipient or pharmaceutical vehicle.

61. A pharmaceutical or veterinary composition comprising as active principle, at least one benzofuran derivative, or a pharmaceutically acceptable salt of the latter, according to claim 29 in combination with an appropriate excipient or pharmaceutical vehicle.

62. A pharmaceutical or veterinary composition comprising as active principle, at least one benzofuran or benzothiophene derivative, or a pharmaceutically acceptable salt of the latter, according to claim 30 in combination with an appropriate excipient or pharmaceutical vehicle.

63. A pharmaceutical or veterinary composition comprising as active principle, at least one benzofuran derivative, or a pharmaceutically acceptable salt of the latter, according to claim 31 in combination with an appropriate excipient or pharmaceutical vehicle.

64. A pharmaceutical or veterinary composition comprising as active principle, at least one benzofuran derivative, or a pharmaceutically acceptable salt of the latter, according to claim 32 in combination with an appropriate excipient or pharmaceutical vehicle.

65. A pharmaceutical or veterinary composition comprising as active principle, at least one benzofuran derivative, or a pharmaceutically acceptable salt of the latter, according to claim 33 in combination with an appropriate excipient or pharmaceutical vehicle.

66. A pharmaceutical or veterinary composition comprising as active principle, at least one benzofuran derivative, or a pharmaceutically acceptable salt of the latter, according to claim 34 in combination with an appropriate excipient or pharmaceutical vehicle.

67. A pharmaceutical or veterinary composition comprising as active principle, at least one benzofuran derivative, or a pharmaceutically acceptable salt of the latter, according to claim 35 in combination with an appropriate excipient or pharmaceutical vehicle.

68. A pharmaceutical or veterinary composition comprising as active principle, at least one benzofuran derivative, or a pharmaceutically acceptable salt of the latter, according to claim 36 in combination with an appropriate excipient or pharmaceutical vehicle.

69. A pharmaceutical or veterinary composition comprising as active principle, at least one benzofuran derivative, or a pharmaceutically acceptable salt of the latter, according to claim 37 in combination with an appropriate excipient or pharmaceutical vehicle.

70. A pharmaceutical or veterinary composition comprising as active principle, at least one benzofuran derivative, or a pharmaceutically acceptable salt of the latter, according to claim 38 in combination with an appropriate excipient or pharmaceutical vehicle.

71. A pharmaceutical or veterinary composition comprising as active principle, at least one benzofuran derivative, or a pharmaceutically acceptable salt of the latter, according to claim 39 in combination with an appropriate excipient or pharmaceutical vehicle.

72. A pharmaceutical or veterinary composition comprising as active principle, at least one benzofuran derivative, or a pharmaceutically acceptable salt of the latter, according to claim 46 in combination with an appropriate excipient or pharmaceutical vehicle.

73. A pharmaceutical or veterinary composition comprising as active principle, at least one benzofuran derivative, or a pharmaceutically acceptable salt of the latter, according to claim 41 in combination with an appropriate excipient or pharmaceutical vehicle.

74. A pharmaceutical or veterinary composition comprising as active principle, at least one benzofuran derivative, or a pharmaceutically acceptable salt of the latter, according to claim 42 in combination with an appropriate excipient or pharmaceutical vehicle.

75. A pharmaceutical or veterinary composition comprising as active principle, at least one benzofuran derivative, or a pharmaceutically acceptable salt of the latter, according to claim 43 in combination with an appropriate excipient or pharmaceutical vehicle.

76. A pharmaceutical or veterinary composition comprising as active principle, at least one benzofuran derivative, or a pharmaceutically acceptable salt of the latter, according to claim 44 in combination with an appropriate excipient or pharmaceutical vehicle.

77. A method for the treatment of pathological syndromes of the cardiovascular system which comprises administering to a patient in need of such treatment an effective amount of a compound according to claim 2.

78. A method for the treatment of pathological syndromes of the cardiovascular system which comprises administering to a patient in need of such treatment an effective amount of a compound according to claim 3.

79. A method for the treatment of pathological syndromes of the cardiovascular system which comprises administering to a patient in need of such treatment an effective amount of a compound according to claim 4.

80. A method for the treatment of pathological syndromes of the cardiovascular system which comprises administering to a patient in need of such treatment an effective amount of a compound according to claim 5.

81. A method for the treatment of pathological syndromes of the cardiovascular system which comprises administering to a patient in need of such treatment an effective amount of a compound according to claim 6.

82. A method for the treatment of pathological syndromes of the cardiovascular system which comprises administering to a patient in need of such treatment an effective amount of a compound according to claim 7.

83. A method for the treatment of pathological syndromes of the cardiovascular system which comprises administering to a patient in need of such treatment an effective amount of a compound according to claim 8.

84. A method for the treatment of pathological syndromes of the cardiovascular system which comprises administering to a patient in need of such treatment an effective amount of a compound according to claim 9.

85. A method for the treatment of pathological syndromes of the cardiovascular system which comprises administering to a patient in need of such treatment an effective amount of a compound according to claim 12.

86. A method for the treatment of pathological syndromes of the cardiovascular system which comprises administering to a patient in need of such treatment an effective amount of a compound according to claim 11.

87. A method for the treatment of pathological syndromes of the cardiovascular system which comprises administering to a patient in need of such treatment an effective amount of a compound according to claim 12.

88. A method for the treatment of pathological syndromes of the cardiovascular system which comprises administering to a patient in need of such treatment an effective amount of a compound according to claim 13.

89. A method for the treatment of pathological syndromes of the cardiovascular system which comprises administering to a patient in need of such treatment an effective amount of a compound according to claim 25.

90. A method for the treatment of pathological syndromes of the cardiovascular system which comprises administering to a patient in need of such treatment an effective amount of a compound according to claim 26.

91. A method for the treatment of pathological syndromes of the cardiovascular system which comprises administering to a patient in need of such treatment an effective amount of a compound according to claim 27.

92. A method for the treatment of pathological syndromes of the cardiovascular system which comprises administering to a patient in need of such treatment an effective amount of a compound according to claim 28.

93. A method for the treatment of pathological syndromes of the cardiovascular system which comprises administering to a patient in need of such treatment an effective amount of a compound according to claim 29.

94. A method for the treatment of pathological syndromes of the cardiovascular system which comprises administering to a patient in need of such treatment an effective amount of a compound according to claim 30.

95. A method for the treatment of pathological syndromes of the cardiovascular system which comprises administering to a patient in need of such treatment an effective amount of a compound according to claim 31.

96. A method for the treatment of pathological syndromes of the cardiovascular system which comprises administering to a patient in need of such treatment an effective amount of a compound according to claim 32.

97. A method for the treatment of pathological syndromes of the cardiovascular system which comprises administering to a patient in need of such treatment an effective amount of a compound according to claim 33.

98. A method for the treatment of pathological syndromes of the cardiovascular system which comprises administering to a patient in need of such treatment an effective amount of a compound according to claim 34.

99. A method for the treatment of pathological syndromes of the cardiovascular system which comprises administering to a patient in need of such treatment an effective amount of a compound according to claim 35.

100. A method for the treatment of pathological syndromes of the cardiovascular system which comprises administering to a patient in need of such treatment an effective amount of a compound according to claim 36.

101. A method for the treatment of pathological syndromes of the cardiovascular system which comprises administering to a patient in need of such treatment an effective amount of a compound according to claim 37.

102. A method for the treatment of pathological syndromes of the cardiovascular system which comprises administering to a patient in need of such treatment an effective amount of a compound according to claim 38.

103. A method for the treatment of pathological syndromes of the cardiovascular system which comprises administering to a patient in need of such treatment an effective amount of a compound according to claim 39.

104. A method for the treatment of pathological syndromes of the cardiovascular system which comprises administering to a patient in need of such treatment an effective amount of a compound according to claim 40.

105. A method for the treatment of pathological syndromes of the cardiovascular system which comprises administering to a patient in need of such treatment an effective amount of a compound according to claim 41.

106. A method for the treatment of pathological syndromes of the cardiovascular system which comprises administering to a patient in need of such treatment an effective amount of a compound according to claim 42.

107. A method for the treatment of pathological syndromes of the cardiovascular system which comprises administering to a patient in need of such treatment an effective amount of a compound according to claim 43.

108. A method for the treatment of pathological syndromes of the cardiovascular system which comprises administering to a patient in need of such treatment an effective amount of a compound according to claim 44.

* * * * *